US006379664B1

(12) United States Patent
Lou et al.

(10) Patent No.: US 6,379,664 B1
(45) Date of Patent: Apr. 30, 2002

(54) COMPOSITION AND METHOD FOR THE PREVENTION AND TREATMENT OF OXIDATIVE DAMAGE IN OCULAR TISSUES

(75) Inventors: Marjorie F. Lou; Nalini Raghavachari; Fengyu Qiao, all of Lincoln, NE (US)

(73) Assignee: Board of Regents University of Nebraska-Lincoln, Lincoln, NE (US)

( * ) Notice: Subject to any disclaimer, the term of this patent is extended or adjusted under 35 U.S.C. 154(b) by 0 days.

(21) Appl. No.: 09/162,564

(22) Filed: Sep. 29, 1998

(51) Int. Cl.$^7$ .......................... A61K 38/45; C12N 9/10
(52) U.S. Cl. ...................... 424/94.5; 435/193; 435/183
(58) Field of Search ................................ 435/193, 183; 424/945

(56) References Cited

U.S. PATENT DOCUMENTS

| | | |
|---|---|---|
| 4,757,063 A | 7/1988 | Parnham .................... 514/183 |
| 4,771,036 A * | 9/1988 | Pigiet et al. .................. 514/17 |
| 4,898,878 A | 2/1990 | Shapiro et al. ............. 514/386 |
| 5,075,116 A | 12/1991 | LaHaye et al. ............. 424/617 |
| 5,112,870 A | 5/1992 | Mao et al. .................. 514/712 |
| 5,401,880 A | 3/1995 | Clark et al. ................. 564/159 |
| 5,591,773 A | 1/1997 | Grunberger et al. ........ 514/532 |
| 5,596,011 A | 1/1997 | Repine et al. .............. 514/369 |
| 5,676,945 A | 10/1997 | Reddy et al. .............. 424/94.5 |
| 5,686,450 A | 11/1997 | Hellberg et al. ......... 514/222.5 |
| 5,688,828 A | 11/1997 | Hellberg et al. ............. 514/565 |
| 5,773,472 A | 6/1998 | Stjernschantz et al. ..... 514/530 |

FOREIGN PATENT DOCUMENTS

| | | |
|---|---|---|
| AU | 97-42195 | 2/1998 |
| WO | WO94/03167 | 2/1994 |

OTHER PUBLICATIONS

Hopper et al. Genbank Accession No: A32682, 1989.*
Padilla et al., High Level expression of fully active human glutaredoxin (thioltransferase) in *E. coli.* and characterization of Cys7 to Ser mutant protein, FEBS 378: 69–73, 1996.*
Yang et al. Genbank Accession No: JQ117, 1987.*
Padilla et al., Genbank Accession No: S68701, 1996.*
Papayannopoulos et al. Genbank Accession No: A30164, 1989.*
WO98/10760 (Mar. 1998), Derwent Abstract.
Lou et al., "A repair mechanism for oxidatively damaged proteins in the lens," 6th Annual Harold Gifford, Jr. Lecture Series, Apr. 3, 1998.
Wu et al., "Distribution of thioltransferase (glutaredoxin) in ocular tissues," *Invest. Ophth. & Vis. Sci.*, vol. 39, No. 3, pp. 476–480, (Mar. 1998).
Wang et al., "Relationship of protein glutathione mixed disulfide and thioltransferase in H2O2–induced cataract in cultured pig lens," *Exp. Eye Res.*, vol. 64, pp. 693–700 (1997).
Raghavachari et al., "Evidence for the presence of thiol-transferase in the lens," *Exp. Eye Res.*, vol. 63, pp. 433–441 (1996).
Raghavachari et al., "Cloning, high level–expression and characterization of human lens thioltransferase," *Exp. Eye Res.*, vol. 66, pp. 465–475 (1998).
Lou et al., "Thioltransferase in present in the lens epithelial cells as a highly oxidative stress–resistant enzyme," Exp. Eye res., vol. 66, pp. 477–486 (1998).

* cited by examiner

*Primary Examiner*—Rebecca E. Prouty
*Assistant Examiner*—Richard Hutson
(74) *Attorney, Agent, or Firm*—Suiter & Associates PC; Scott C. Rand; William J. Breen, III

(57) ABSTRACT

Thioltransferase and derivatives thereof are provided. Methods of treating or preventing cataract formation comprising administering thioltransferase or a derivative thereof are also provided. Thioltransferase or derivatives thereof are also useful for treating or preventing diseases resulting from or associated with oxidative stress. Human lens thioltransferase and a DNA sequence encoding the same are also provided.

24 Claims, 10 Drawing Sheets

```
GCCATGGCTC AAGAGTTTGT GAACTGCAAA ATCCAGCCTG GGAAGGTGGT AGTTTTCATC  (60)
   MetAlaG lnGluPheVa lAsnCysLys IleGlnProG lyLysValVa lValPheIle  (19)

AAGCCCACCT GCCCCTTCTG CGTAAAGACA CAGGAGCTCC TCAGCCAATT GCCCTTCAAA (120)
LysProThrC ysProPheCy sValLysThr GlnGluLeuL euSerGlnLe uProPheLys  (39)

GAAGGGCTTC TGGAATTTGT CGATATTACA GCCACCAGTG ACACCAACGA GATTCAAGAT (180)
GluGlyLeuL euGluPheVa lAspIleThr AlaThrSerA spThrAsnGl uIleGlnAsp  (59)

TATCTGCAAC AGCTCACAGG AGCCAGAACG GTACCTCGGG TCTTTATCGG TAAAGAGTGT (240)
TyrLeuGlnG lnLeuThrGl yAlaArgThr ValProArgV alPheIleGl yLysGluCys  (79)

ATAGGTGGAT GCACTGATCT AGAAAGTATG CACAAGAGAG GGGAGCTCTT GACCCGCCTG (300)
IleGlyGlyC ysThrAspLe uGluSerMet HisLeuArgG lyGluLeuLe uThrArgLeu  (99)

CAGCAAATTG GAGCTCTGAA ATAATTACAG CAGAGCAGAC CCAAGCTGAT AGCTCCCTTG (360)
GlnGlnIleG lyAlaLeuLy s                                           (106)

AGAGCTGGAT GGCAGTGCAG ATAATGACAG CGCTTCCTGG TGGATGGATG CCGGGCTACC (420)

TTCACTCAGC TGCAACTACT GTTTACTTAA AAATTCTGAA ATGTGTTAAC CCAAATAATT (480)

GGGGGGAGTG GGTTTTGGGG GACAAAACAG ATTTTTCTTC TG                    (520)
```

FIG. 1

```
                   10         20         30         40         50         60
A: MAQEFVNCKI QPGKVVVFIKPT CPFC* VKTQELLSQLPFKEGLLEFVDITATSDTNEIQDYL
B: MAQAFVNSKI QPGKVVVFIKPT CPFC* RKTQELLSQLPFKEGLLEFVDITATSDTNEIQDYL
C: MAQEFVNCKI QPGKVVVFIKPT CPYC* RRAQEILSQLPIKQGLLEFVDITATNHTNEIQDYL
D: MAQAFVNSKI QPGKVVVFIKPT CPYC* RKTQELLSQLPFKQLLEFVDITAAGNISEIQDYL
E: MAQEFVNSKI QPGKVVVFIKPT CPYC* RKTQEILSQLPFKQGLLEFVDITATSDMSEIQDYL
                  10         20         30         40         50
F:           MQTVIFGRSG CPYC* VRAKDLAEKLSNERDDFQYQYVDIRAEGITKEDLQQ 70           80              90         100
A: QQLTGAR TVP RVFIGKEC IGGCTD* LESMHK RGELLTRLQQIGALK
B: QQLTGAR TVP** RVFIGKEC IGGCTD*** LESMHK RGELLTRLQQIGALK
C: QQLTGAR TVP** RVFIGKDC IGGCTD*** LVSLQQSGELLTRLKQIGALQ
D: QQLTGAR TVP** RVFIGQEC IGGCTD*** LVNMHIE RGELLTRLKQMGALQ
E: QQLTGAR TVP** RVFLGKDC IGGCSD*** LIAMQEKGELLARLKEMGALRQ
          60            70              80
F: KAGKPVE TVP** QIFVDQQH IGGYTD*** FAAWVKENLDA
```

FIG. 2

COMPOSITION AND METHOD FOR THE PREVENTION AND TREATMENT OF OXIDATIVE DAMAGE IN OCULAR TISSUES

GOVERNMENT RIGHTS

This invention was made in part with government support under grant number R01-10595 awarded by the National Eye Institute. The government has certain rights in the invention.

BACKGROUND OF THE INVENTION

In one aspect, the present invention relates generally to the field of ophthalmology and, more particularly, to compositions and methods for the prevention or treatment of eye diseases, such as cataracts. In another aspect, the present invention relates to the prevention or treatment of diseases caused by oxidative stress or having oxidative stress as a component.

The lens consists of concentric layers of fiber cells with hexagonal cross sections packed together to create a very regular array of fiber cells which stretch from anterior to posterior pole. The lens fiber cells lose all intracellular organelles that could contribute to light scattering during the process of differentiation and the cytoplasmic protein concentration increases markedly. Lens transparency is the result of a uniform structure of the cells' cytoplasm, which exists in an ordered, homogeneous state.

Approximately 35% to 60% of the total mass of the lens consists of structural proteins with the remainder being water. These cells contain primarily the crystallin proteins. When these proteins are modified by oxidative stress, conformational changes and aggregates result which, in turn, disrupt the protein lattice and damage the cell. This cellular damage leads to a further disruption of the regular layers of cells, resulting in opacities, or cataracts, of the lens.

More than 90% of the total lens protein consists of alpha, beta, and gamma crystallins (in excess of 300 mg/ml) in the lens cell cytoplasm. Crystallins are proteins containing numerous sulfhydryl groups, making them susceptible to oxidative damage. Protein S-thiolation, the formation of mixed disulfides between non-protein thiols and protein sulfhydryl groups in the lens, is an early event under oxidative damage (Lou et al., "The role of protein thiol mixed disulfides in cataractogenesis," *Exp. Eye Res.*, vol. 50, 819–26 (1990)). Protein-glutathione (PSSG) and protein-cysteine (PSSC) are the products of such protein modification that have been implicated as a direct precursor of protein-protein disulfides (PSSP) in rat lenses cultured with $H_2O_2$. These changes ultimately lead to protein insolubility, loss of transparency of the lens tissue, and cataract formation (Cui et al., "The effect and recovery of long term $H_2O_2$ exposure on lens morphology and biochemistry," *Exp. Eye Res.*, vol. 57, 157–67 (1993)).

In unstressed normal cells, the concentration of S-thiolated proteins is very low and the dethiolation rate, i.e., the breakdown of mixed disulfides by reduction of disulfide bonds, may be sufficient to maintain the fully reduced protein status. Such a situation has been observed in the $H_2O_2$ pre-exposed lenses after the oxidant was removed from the culture medium (Cui et al., *Exp. Eye Res.*, vol. 57, 157–67 (1993); Lou et al., "Further studies on the dynamic changes of glutathione and protein-thiol mixed disulfides in $H_2O_2$ induced cataract in rat lenses: distributions and effect of aging," *Curr. Eye Res.*, vol. 14, 951–58 (1995)). This implies that the maintenance of the redox status of the sulfhydryl groups of the protein is vital to the physiological function of the lens, a tissue abundant in sulfhydryl groups and extremely vulnerable to oxidative damage.

The redox state of the cell is maintained by many reductants, such as glutathione (GSH), NADPH, ascorbate, and tocopherol (Spector, "The lens and oxidative stress," in *Oxidative Stress, Oxidants, and Antioxidants* (Sies, Ed.) pp. 529–58, Academic Press: London (1991)). Among these reductants, GSH has a significant role in maintaining the reduced condition of the cell. Traditionally, GSH with glutathione reductase has been viewed as the system responsible for maintaining and regenerating the protein thiol groups that are susceptible to oxidation. Reduced GSH and other thiol containing molecules act, at least indirectly, as oxygen free radical scavengers, due to their easily oxidizable sulfhydryl groups and hence act as sulfhydryl antioxidants in normal lenses. Glutathione reductase regenerates GSH from its disulfide oxidized form (GSSG) and acts as a sulfhydryl buffering system, continually controlling the sulfhydryl/disulfide balance in the cell. GSH exists in great excess of its GSSG oxidized counterpart in the cellular cytoplasm, thus creating a strong potential for cytosolic proteins to exist in a sulfhydryl-reduced, non-crosslinked state. Deficiencies of GSH have been observed in cataractous lenses (*Biochim et Biophys Acta*, vol. 1138, 11–19 (1992)). This deficiency leads to a reduced ability of the cell to repair damage associated with oxidative stress.

Antioxidant therapy has been proposed to ameliorate the destructive effects of oxidation resulting in the formation of cataracts (*American J. of Clinical Nutrition*, vol. 53, pp.335S–345S (1991) and pp.352S–355S (1991)). Such proposed therapy has included the systemic administration of vitamins C and E and beta carotene. The use of phenolic antioxidants, such as probucol, to inhibit the development of cataracts, is disclosed in U.S. Pat. No. 5,061,734 to Mao et al. The use of N,N'-bis(mercaptoacetyl)hydrazine derivatives as anticataract agents is disclosed in U.S. Pat. Nos. 5,686,450 and 5,688,828, both to Hellberg et al. PCT Application No. WO 94/03167 discloses the use of N-(3-mercapto-2,2-dimethylpropanoyl)cysteine and the intramolecular disulfide thereof for the treatment of cataract. Alpha-lipoic acid is disclosed as an anticataract agent in Maitra et al., "Alpha-Lipoic Acid Prevents Buthionine Sulfoximine-Induced Cataract Formation in Newborn Rats," *Free Radical Biology and Medicine*, vol. 18, pp. 823–829 (1995). The use of phase separation inhibitors is proposed in U.S. Pat. No. 5,401,880 to Clark et al.

Cataracts are the leading cause of blindness in humans, with more than one million cataract extractions performed each year in the United States and with an estimated 5 to 10 million people becoming visually disabled each year due to cataracts. Cataracts in animals also pose a significant veterinary problem. Currently, no accepted nonsurgical therapy for the prevention and treatment of cataracts exists. Although various drugs have been proposed for use in the treatment and prevention of cataracts, it would be desirable to avoid potential adverse effects, such as chemical related toxicity, of such compounds.

SUMMARY OF THE INVENTION

The present invention is directed to compositions and methods for preventing or delaying the onset of cataracts and for treating or inhibiting the progression of cataracts in animals through the administration of thioltransferase (glutaredoxin) or derivatives thereof. In another aspect, the present invention is directed to the prevention and treatment of oxidative stress or damage and disease states associated therewith through the administration of thioltransferase or derivatives thereof. In one embodiment the animal may be a mammal. When the animal is a mammal, it may be a human.

The present invention is based on our discovery of the presence of thioltransferase in the lens and other ocular tissues, including the cornea cells, iris, and retina, all vulnerable to oxidative damage. Thioltransferase has been found by us to be an intrinsic repair system capable of dethiolating mixed disulfides associated with cataract initiation and formation, and thus is capable of repairing damaged proteins and nonprotein thiols by restoring them to their respective normally reduced states. It has also been found by us that thioltransferase can dethiolate enzymes damaged by thiolation, thus reactivating the catalytic function of the enzymes. Because thioltransferase in an endogenous biomolecule, it will cause no adverse effects due to chemical related toxicity.

BRIEF DESCRIPTION OF THE DRAWINGS

The detailed description of the invention may be best understood when read in reference to the accompanying drawings wherein:

FIG. 1 shows the nucleotide and the deduced amino acid sequence of the coding region of the human lens thioltransferase;

FIG. 2 shows the alignment of the deduced amino acid sequence of thioltransferases;

DETAILED DESCRIPTION OF THE INVENTION

Figure 3A:
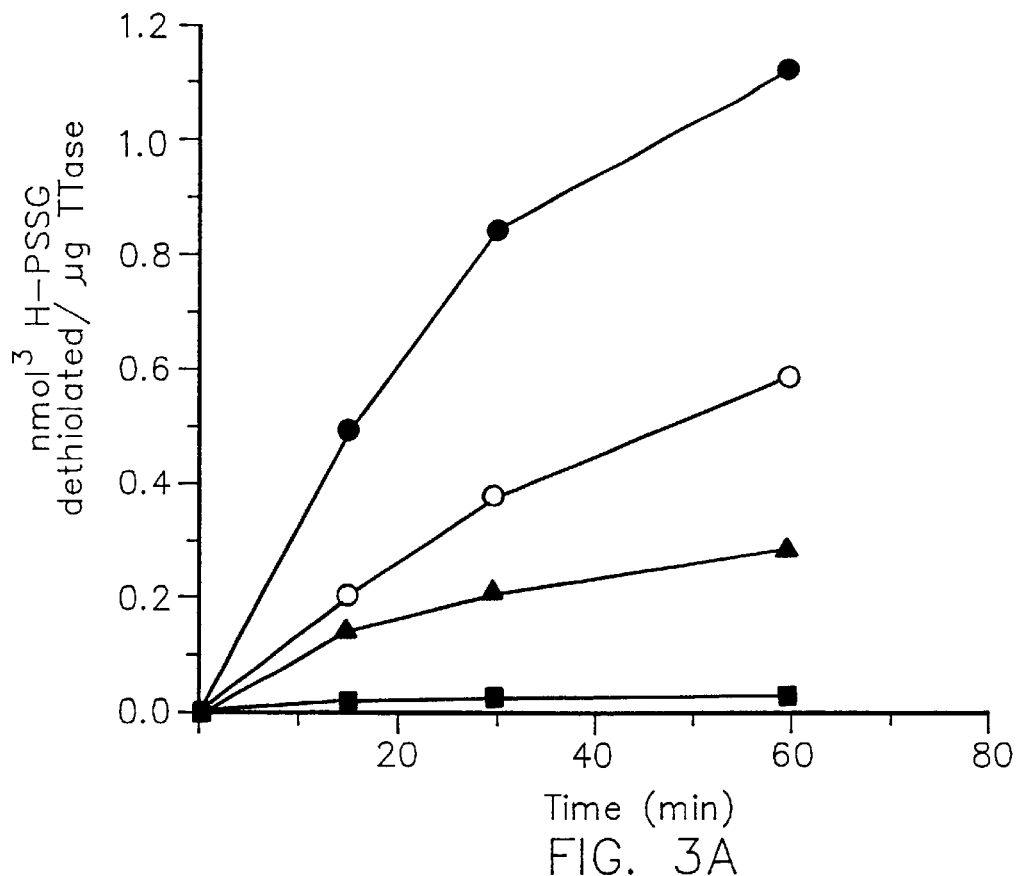
FIGS. 3A and 3B show the time dependent dethiolation in the presence and absence of HLTT.

Thioltransferase acts as a repair enzyme under oxidative stress to prevent lens protein aggregation by protecting thiol groups from oxidation and restoring thiolated proteins to their normal reduced state by cleaving protein-thiol mixed disulfides, thus preventing protein-protein disulfide crosslinking. Thioltransferase also acts as a primary antioxidant by protecting the lens from oxidation by its ability to regenerate ascorbic acid, an important free radical scavenger.

In a first aspect, the present invention provides a method of inhibiting the formation of a cataract in an eye of a subject, which comprises administering to the subject a pharmaceutical composition comprising an effective cataract inhibiting amount of a thioltransferase or thioltransferase derivative. The pharmaceutical composition preferably further comprises a pharmaceutically acceptable carrier in accordance with formulation techniques known to those skilled in the art.

As used herein, the term "pharmaceutically acceptable carrier" encompasses any of the standard pharmaceutically acceptable carriers known to those skilled in the art. Examples of such standard carriers include, but are not limited to, phosphate buffered saline (PBS) solution, water, emulsions such as water/oil emulsions or a triglyceride emulsion, various types of wetting agents, tablets, enteric coated tablets and capsules, and so forth.

The thioltransferase may be any naturally occurring thioltransferase, including, but not limited to mammalian derived thioltransferases. Exemplary mammalian thioltransferases include, but are not limited to, human, pig, cow, and rabbit thioltransferases. Also contemplated are tissue specific variants, such as liver, RBC, placental, and ocular thioltransferases, and so forth. Other thioltransferases are also contemplated, such as thioltransferase derived from *E. coli*. In a preferred embodiment, the thioltransferase is human lens thioltransferase as defined by SEQ ID NO:1.

In the above described methods of inhibiting the formation of cataracts in an eye, the eye may already contain one or more developing or fully developed cataracts before it is contacted with the thioltransferase or derivative thereof. Accordingly, the above disclosed method can be used to inhibit the formation of further cataracts in the eye, to inhibit the progression of any developing cataracts already present in the eye, or to at least partially reverse the development of such mature or developing cataracts in the eye. Alternatively, the eye may be free of any developing or fully developed cataracts when it is contacted with the thioltransferase or derivative thereof.

Any suitable means known to those skilled in the art may be used to administer the pharmaceutical composition to the subject in accordance with the present invention. The composition may be administered systemically, or, in a preferred embodiment, is administered to the eye by directly applying the composition to the eye.

In another aspect, the present invention provides pharmaceutical compositions comprising the thioltransferase or derivatives thereof according to the present invention. Any suitable means may be used to administer the pharmaceutical compositions to a subject in accordance with the present invention. Formulations for the thioltransferase or derivatives thereof according to the present invention may be any conventional formulation for protein or peptide drugs, such as found in *Remington's Pharmaceutical Sciences*, latest edition (Mack Publishing Co.: Easton, Pa.). Typically, proteins and peptides are administered by injection, such as intravenous, intramuscular, subcutaneous, or intraperitoneal injection, or using formulations for transmucosal or transdermal delivery. These formulations generally include a detergent or penetrant such as bile salts, fusidic acids, and the like. The pharmaceutical composition may be injected into any part of the subject's body, including into one or both of the subject's eyes. These formulations may also be administered as aerosols or suppositories. In the case of transdermal administration, the formulation may be in the form of a topical ointment, lotion, cream or skin patch, and may include a transdermal agent. For systemic application, the pharmaceutical composition may be applied to any part of the subject's body. The compositions according to the present invention may be adapted for oral administration, i.e., in the form of tablets, capsules, solutions, suspensions, and other dosage forms adapted for oral administration, provided the formulation protects the thioltransferase or derivatives thereof according to the present invention from degradation in the digestive system. Optimization of dosage regimen and formulation is conducted as a routine matter and as generally performed in the art. Although thioltransferase is generally a heat stable enzyme, it should be stored at a cold temperature.

In a preferred embodiment, the eye is contacted directly with the thioltransferase or derivative thereof. Any suitable means known to those skilled in the art may be used to contact the eye with the thioltransferase or derivative thereof. Examples of such methods include, but are not limited to, injection into the eye, or, dropping, spraying, or other topical application to the eye. Vehicles for topical ophthalmic formulations are generally known to those skilled in the art. Various electrolytes, solvents, co-solvents, surfactants, preservatives or antimicrobial agents, viscosity building agents, etc., are taught in U.S. Pat. No. 5,686,450, incorporated herein by reference in its entirety.

As used herein, the term "effective cataract-inhibiting amount" is intended to encompass any amount which will inhibit the progression or formation of cataracts in an eye. The route of administration and the dosage regimen will be determined by skilled clinicians. As such, the effective cataract-inhibiting amount of the compound will depend on various factors known to those skilled in the art, which include, but are not limited to, the size of the eye, the exact nature and severity of the condition being treated such as the number and progression of any mature or developing cataracts already present invention eye, whether the eye is to be contacted a single time or periodically over a period of time and the length of such period of time. The period of time may be any number of days, weeks, months, or years. In one embodiment, the thioltransferase or derivative thereof is administered from one to four times per day until the desired results have been achieved. In one embodiment, the effective cataract-inhibiting amount of the thioltransferase or derivative thereof is an amount that provides a given level of enzyme activity in the lens. A typical lens (old lens, i.e., 65 years or older) weighs about 200 mg and about 30% of the weight are proteins. The enzyme activity in a typical old human lens is about 50.6 mUnit or about $1.2 \times 10^{-3}$ Unit activity per mg lens protein.

For direct administration to the eye, the dosage may be an amount which provides an enzyme activity of about $1.2 \times 10^{-3}$ Unit activity per mg lens protein or higher. In another embodiment, the dosage may be an amount that provides an activity of one to several, or more, orders of magnitude higher than $1.2 \times 10^{-3}$ Unit activity per mg lens protein. In one embodiment, the dosage may be an amount that provides an activity of about 1.2 Unit activity per mg lens protein or higher. In another embodiment, the dosage may be an amount that provides an activity of about $1.2 \times 10^3$ Unit activity per mg lens protein or higher.

For systemic administration, the dosage is an amount that provides an activity of $1.2 \times 10^{-3}$ Unit activity per mg lens protein or higher. In another embodiment, the dosage may be an amount that provides an activity of one to several, or more orders of magnitude higher than $1.2 \times 10^{-3}$ Unit activity per mg lens protein. In one embodiment, the dosage may be an amount that provides an activity of about 1.2 Unit activity per mg lens protein or higher. In another embodiment, the dosage may be an amount that provides an activity of about $1.2 \times 10^3$ Unit activity per mg lens protein or higher. It will be understood that to achieve the desired level of activity in the lens, a dose administered systemically will generally be higher than a dose administered directly to the eye.

In another embodiment, the administration of thioltransferase or a derivative thereof may comprise surgically removing the lens of the eye from the subject, applying the thioltransferase or derivative thereof to the lens, and then surgically replacing the lens.

In one embodiment of the above described method, the subject is a mammal. When the subject is a mammal, the subject may be a human being.

This invention further provides treatment, prevention, or inhibiting the progression of other eye diseases, including, but not limited to, glaucoma, macular degeneration, uveitis, iritis, cornea inflammation (either by injury or disease) or other trauma to the eye. Also, this invention further provides a method of treating, preventing, or inhibiting the progression of a disease, in a subject, resulting from oxidative stress which comprises administering to the subject a pharmaceutical composition comprising an effective oxidative stress inhibiting amount of thioltransferase or derivative thereof. As used herein, a disease resulting from oxidative stress is any disease resulting from the effects of reactive oxygen species generated in cells. Reactive oxygen species include superoxide ($O_2^-$.), $H_2O_2$, hydroxyl (OH.) radicals, and singlet oxygen (O.). Reactive oxygen species may be generated in cells during aerobic cellular metabolism. For example, $O_2$ is converted to superoxide by oxidative enzymes in the endoplasmic reticulum, mitochondria, plasma membrane, peroxisomes, ctyosol, and so forth. Superoxide is converted to $H_2O_2$ by dismutation and thence to hydroxyl by the $Fe^{++}/Cu^{++}$ catalyzed Fenton reaction or through the Haber-Weiss reaction. $H_2O_2$ is also derived directly from oxidases in peroxisomes. Reactive oxygen species may also be initiated within cells by absorption of radiant energy such as x-rays, ultraviolet light, or other ionizing radiation. Reactive oxygen species may also be produced by reaction of other free radicals, metabolism of chemicals, drugs, chemotherapuetic agents, pesticides, cigarette smoke, and fatty foods.

Diseases which may result from oxidative stress are generally known to those skilled in the art, and include, but are not limited to, rheumatoid arthritis, lupus, sickle cell anemia, sickle cell disease, the effects of aging, lipid peroxidation of membranes, glycosylation of proteins, oxidative modification of proteins, including sulfhydryl mediated cross linking, fragmentation of polypeptide chains, and enzyme degradation. Oxidative stress causes oxidation of DNA and damages DNA in cells. Such damage may lead to the formation of tumors. Thus, diseases which result from oxidative stress include diseases which comprise the formation of tumors resulting from oxidative stress. Diseases which comprise the formation of tumors include cancer. For example, reactions with thymine in DNA produce single stranded breaks in DNA. Such DNA damage has been implicated not only in cell death, but also, in eventual malignant transformation of cells. Mitochondrial DNA is also affected by oxidative stress.

Other diseases which may result from oxidative stress include diseases coronary and/or circulatory system, diseases of the central nervous system (CNS), inflammatory diseases, diseases of the pulmonary system, protein condensation diseases, and other diseases. Such diseases include myocardial infarction, stroke, angina, atherosclerosis, ischemic disease, reperfusion injury, hypercholesterolemia, adhesion formation, glaucoma, idiopathic pulmonary fibrosis, chronic renal failure, nephrolithiasis, nephrosclerosis, gastric ulcer, cholesterol gallstone disease, hepatitis, epilepsy and Parkinson's disease, Alzheimer's disease, asthma, psoriasis, multiple myeloma, and side effects of drugs such as anticancer drugs, side effects of radiation, and so forth. Thioltransferase or derivatives thereof may also be for the treatment of diabetes and complications thereof such as diabetic cataract, diabetic retinopathy, neuropathy, nephropathy, and neovascularization of the cornea or retina.

The compositions comprising thioltransferase or derivatives thereof preferably further comprise one or more pharmaceutically acceptable carriers as described above which includes, but is not limited to, PBS, water, emulsions such as oil/water emulsions or triglyceride emulsions, various types of wetting agents, oral formulations, and so forth. A pharmaceutically acceptable carrier may be selected taking into account the desired mode of administration.

Any suitable means known to those skilled in the art may be used to administer the pharmaceutical composition to the subject in accordance with the present invention. The composition may be administered systemically, or, in a preferred embodiment, is administered to the location of oxidative stress.

In another aspect, the present invention provides pharmaceutical compositions comprising the thioltransferase or derivatives thereof according to the present invention. Any suitable means may be used to administer the pharmaceutical compositions to a subject in accordance with the present invention. Formulations for the thioltransferase or derivatives thereof according to the present invention may be any conventional formulation for protein or peptide drugs, such as found in *Remington's Pharmaceutical Sciences* (Mack Publishing Co.: Easton, Pa.). Proteins and peptides may advantageously be administered by injection, such as intravenous, intramuscular, subcutaneous, or intraperitoneal injection, or using formulations for transmucosal or transdermal delivery. These formulations generally include a detergent or penetrant such as bile salts, fusidic acids, and the like. The pharmaceutical composition may be injected into any part of the subject's body, including one or both of the subject's eyes. These formulations may also be administered as aerosols or suppositories. In the case of transdermal administration, the formulation may be in the form of a topical ointment, lotion, cream or skin patch, and may include a transdermal agent. For systemic application, the pharmaceutical composition may be applied to any part of the subject's body. The compositions according to the present invention maybe adapted for oral administration, i.e., in the form of tablets, capsules, solutions, suspensions, and other dosage forms adapted for oral administration, provided the formulation protects the thioltransferase or derivatives thereof according to the present invention from degradation in the digestive system. Optimization of dosage regimen and formulation is conducted as a routine matter and as generally performed in the art. Although thioltransferase is generally a heat stable enzyme, it should be stored at a cold temperature.

In the above described method of treating or preventing a disease resulting from oxidative stress, any suitable means known to those skilled in the art may be used to administer the thioltransferase or derivative thereof to the subject. In one embodiment a pharmaceutical composition comprising thioltransferase or a derivative thereof is administered topically to a part of the subject's body where oxidative stress is expected to occur, is likely to occur, or may occur. In another embodiment, a pharmaceutical composition comprising thioltransferase or a derivative thereof is administered topically to a part of the subject's body where oxidative stress has occurred. It will be recognized, however, that topical application to one part of a subject's body can be expected to have beneficial systemic effects on other parts. Where topical application is used, the composition may be in the form of a cream or lotion and may include a transdermal agent.

In yet another embodiment, a pharmaceutical composition comprising thioltransferase or a derivative thereof is orally administered to the subject. If oral administration is employed, the composition may be in the form of a capsule, tablet, suspension, solution, and so forth.

When treating any of the above mentioned eye disorders, an ophthalmic formulation as detailed above may advantageously be employed.

In another embodiment, a pharmaceutical composition comprising thioltransferase or a derivative thereof may be injected into the subject. Injection may be intramuscular, intraperitoneal, intravenous, or subcutaneous. The pharmaceutical composition may be injected into any part of the subject's body, including the part of the body where oxidative stress has occurred or is expected to occur, is likely to occur, or may occur.

As used herein, an "effective oxidative stress inhibiting amount" is intended to encompass an amount of thioltransferase or derivative thereof which will inhibit the generation of reactive oxygen species in cells. The route of administration and the dosage regimen will be determined by skilled clinicians. As such, the effective oxidative stress inhibiting amount will depend on various factors known to those skilled in the art. Such factors include, but are not limited to, the size of the subject, the mode of administration, the exact nature and severity of the condition being treated, whether the thioltransferase or derivative thereof is to be administered a single time or periodically over a period of time and the length of such period of time. The period of time may be any number of days, weeks, months, or years. In one embodiment, the thioltransferase or derivative thereof is administered from one to four times per day until the desired results have been achieved. In one embodiment, the effective oxidative stress inhibiting amount of the thioltransferase or derivative thereof is an amount that provides a given level of enzyme activity in the affected area.

For direct administration of the compositions according to the present invention to the affected area, the dosage may be an amount sufficient to provide a normal physiological level of activity or higher. In another embodiment, the dosage is an amount which provides an activity level which is from one to several, or more, orders of magnitude higher than the normal physiological level of activity. In still another embodiment, the dosage is an amount which provides an activity level which is three or more orders of magnitude higher than the normal physiological level of activity. In another embodiment, the dosage is an amount which provides an activity level which is six or more orders of magnitude higher than the normal physiological level of activity. In yet another embodiment, the dosage is an amount which provides an activity of about $1.2 \times 10^{-3}$ Unit activity per mg protein in the affected area or higher. In another embodiment, the dosage may be an amount that provides an activity of one to several, or more, orders of magnitude higher than about $1.2 \times 10^{-3}$ Unit activity per mg protein. In one embodiment, the dosage may be an amount that provides an activity of about 1.2 Unit activity per mg protein or higher. In still another embodiment, the dosage may be an amount that provides an activity of about $1.2 \times 10^3$ Unit activity per mg protein or higher.

For systemic administration, the dosage may be an amount sufficient to provide a normal physiological level of activity or higher in the affected area. In another embodiment, the dosage is an amount which provides an activity level which is one to several, or more, orders of magnitude higher than the normal physiological level of activity. In another embodiment, the dosage is an amount which provides an activity level which is three or more orders of magnitude higher than the normal physiological level of activity. In another embodiment, the dosage is an amount which provides an activity level which is six or more orders of magnitude higher than the normal physiological level of activity. In another embodiment, the dosage is an amount which provides an activity of about $1.2 \times 10^{-3}$ Unit activity per mg protein in the affected area or higher. In another embodiment, the dosage may be an amount that provides an activity of one to several, or more, orders of magnitude higher than $1.2 \times 10^{-3}$ Unit activity per mg protein. In one embodiment, the dosage may be an amount that provides an activity of about 1.2 Unit activity per mg protein or higher. In another embodiment, the dosage may be an amount that provides an activity of about $1.2 \times 10^3$ Unit activity per mg protein or higher. It will be understood that to achieve the desired level of activity in the affected area, a dose administered systemically will generally be higher than a dose administered directly to the affected area. For treatment of the eye disease other than cataracts, the dosages and regimens, formulation, and administration methods employed may generally be comparable to those detailed above for treatment of cataracts.

In one embodiment of the above described method of preventing or inhibiting the progression of a disease caused by oxidative stress, the subject maybe a mammal. When the subject is a mammal, the subject may be a human being.

In one embodiment according to the present invention, the thioltransferase is human lens thioltransferase (HLTT). When the thioltransferase is HLTT, the HLTT may be recombinant human thioltransferase (RHLT) according to the amino acid sequence set forth in SEQ ID NO:2.

In an alternative embodiment, the thioltransferase may be another thioltransferase as described above, including, but not limited to, the thioltransferases depicted in SEQ ID NOS:3–7.

In another embodiment, the thioltransferase may be any isomer or isoenzyme (isozyme) of HLTT or any isomer or isozyme of thioltransferase from other organisms, including tissue specific thioltransferases. Tissue specific thioltransferases include, but are not limited to, thioltransferases from ocular tissues, RBC, liver, placenta, and so forth.

In another embodiment, the thioltransferase may be a thioltransferase derivative. Proteins useful as thioltransferase derivatives include proteins or polypeptides having an amino acid sequence substantially homologous to at least a portion of the amino acid sequence set forth in any of amino acid sequences set forth in SEQ ID NOS:2–7, preferably SEQ ID NO:2. The term "homologous" refers to the one to one correlation between the sequences of two polypeptides. It will be recognized by those skilled in the art that 100% homology is not required in all cases and the present invention is intended to encompass thioltransferase derivatives which are substantially homologous to human lens thioltransferase or other thioltransferases. Substantial homology requires only that the essential nature of the polypeptide, i.e., folding characteristics and unique features such as the active site or other critical regions are preserved. Thus, modifications of thioltransferase are anticipated and are within the scope of the present invention. Such modifications may be deliberate, as through site directed mutagenesis, or may be accidental as through mutations in hosts which are producers of the thioltransferase.

In some embodiments of the present invention, the thioltransferase derivatives may be at least about 75% homologous to the sequence of a known wild type or native thioltransferase, including those set forth in SEQ ID NOS:3–7, or in a preferred embodiment, may be at least about 75% homologous to the sequence of native HLTT set forth in SEQ ID NO:2. In other embodiments of the present invention, the thioltransferase derivatives may be at least about 85% homologous to the sequence of a known native thioltransferase, including those set forth in SEQ ID NOS:3–7, or in a preferred embodiment, may be at least about 85% homologous to the sequence of native HLTT set forth in SEQ ID NO:2. In yet other embodiments of the present invention, the thioltransferase derivatives may be at least about 95% homologous to the sequence of a known native thioltransferase, including those set forth in SEQ ID NOS:3–7, or in a preferred embodiment, may be at least about 95% homologous to the sequence of native HLTT set forth in SEQ ID NO:2. It is also anticipated that certain non-commonly occurring amino acids may be substituted for commonly occurring counterparts to confer desirable characteristics to the resulting polypeptide.

Furthermore, it is contemplated in some aspects of the present invention that thioltransferase derivatives may encompass polypeptides that comprise only a portion of the sequence of thioltransferase, such as known thioltransferases including those listed in SEQ ID NOS:3–7 and, in a preferred embodiment, thioltransferase derivatives may encompass polypeptides that comprise only a portion of the sequence of HLTT set forth in SEQ ID NO:2. This may be the case, for example, for a chimeric protein encompassing active or otherwise desirable portions of a number of proteins. A portion may also refer to a truncated polypeptide, be it substantially truncated or only slightly truncated. Such truncated polypeptides may be the result of an idiosyncracy in the mode of production which results in truncation of amino acids from a terminal end, or a finding that the truncated polypeptide has activity similar to or better than the full-length protein. Preferably, such truncations should not remove regions critical for biological activity. In a preferred embodiment, such truncated polypeptides may include, for example, truncated proteins containing the three highly conserved regions as set forth in FIG. 2. It is contemplated that there may be other critical regions as well, e.g., regions necessary for inducing proper folding and proper three-dimensional conformation, catalytic activity, and the like. The ascertainment of noncritical regions is readily accomplished by deleting or modifying candidate regions and conducting an appropriate assay for thioltransferase activity. Regions where modifications result in a loss of activity are critical; regions wherein the alteration results in the same or similar activity are considered noncritical.

Of course, in still other aspects of the present invention, the full length protein, as set forth in SEQ ID NO:2, is contemplated.

The thioltransferase or derivative thereof according to the present invention, depending on the pH of its environment, if suspended or in solution, or of its environment when crystallized or precipitated, if in solid form, may be in the form of pharmaceutically acceptable salts or may be in neutral form. The free amino groups of the protein are, of course, capable of forming acid addition salts with, for example, inorganic acids, such as, for example, hydrochloric, phosphoric, or sulfuric acid; or with organic acids such as, for example, acetic, glycolic, succinic, mandelic acid, and so forth. The free carboxyl groups are capable of forming salts with bases, including inorganic bases such as sodium, potassium, or calcium hydroxides, and organic bases, such as piperidine, glucosamine, trimethylamine, choline, and caffeine. In addition, the protein may be modified by combination with other biological materials, such as lipids and saccharides, or by side chain modifications, such as acetylation of amino groups, phosphorylation of hydroxy side chains, or oxidation of sulfhydryl groups.

The thioltransferase or derivatives thereof according to the present invention are preferably purified and isolated. As used herein, "purified" and "isolated" are intended to refer to molecules which have been purified or synthesized so as to be substantially homogeneous. It will be recognized that the terms do not exclude the possibility that certain impurities may be present in the composition so long as the essential nature of the protein is intact.

In another aspect, the present invention pertains to a DNA sequence which encodes HLTT, which includes a DNA segment that can express the gene encoding HLTT, comprising the nucleotide sequence of SEQ ID NO:1. Also contemplated is a DNA sequence which comprises a DNA segment analogous to the nucleotide sequence of SEQ ID NO:1 wherein analogous DNA segment differs from the nucleotide sequence of SEQ ID NO:1 wherein one or more bases are replaced by other bases by means of the degeneracy of the genetic code without altering the corresponding amino acid sequence. Contemplated in yet another embodiment are DNA sequences which hybridize with the nucleotide sequence of SEQ ID NO:1 or a fragment thereof, wherein said DNA segment encodes a polypeptide having thioltransferase activity. In still another embodiment, a DNA segment encoding thioltransferase derivatives as defined above, including homologous amino acid sequences and truncated amino acid sequences.

The present invention also provides a recombinant vector comprising the above mentioned DNA sequences. In another embodiment, the present invention provides an expression vector comprising the above mentioned DNA sequences. As is well known, expression systems are now available compatible with a wide variety of hosts, including procaryotic hosts such as bacteria and eucaryotic hosts such as yeast, plant cells, insect cells, mammalian cells, avian cells, and the like. In still another embodiment, the present invention provides transformed cells obtained by introducing into a host cell a replicable recombinant DNA which comprises a self-replicable vector and a DNA sequence as set forth in SEQ ID NO:1 or other DNA sequence as described above. Transformed host cells may be any host cell which has been altered to contain an expression system according to the present invention by any convenient manner of introducing it, including transfection, viral infection, electroporation, and so forth. In a preferred embodiment, the host cell is $E.$ $coli.$ The present invention also provides a process for producing a recombinant HLTT (RHLT), which comprises culturing the above described transformant to produce RHLT and collecting the RHLT from the resultant culture. Any conventional means for recovery of the protein may be employed. For example, the protein produced may be recovered from the lysate of the cells if produced intracellularly, or from the medium if secreted. Techniques for recovering recombinant proteins from cell cultures are well understood in the art, and the proteins can be purified using known techniques such as chromatography, gel electrophoresis, selective precipitation, and the like.

Human lens thioltransferase can be prepared according to the method disclosed in Raghavachari et al., "Cloning, high-level expression, and characterization of human lens thioltransferase," $Exp.$ $Eye$ $Res.,$ vol. 66, pp. 465–475 (1998), herein incorporated by reference in its entirety. Also incorporated by reference in its entirety is Lou et al., "Thioltransferase is present in the lens epithelial cells as a highly oxidative stress-resistant enzyme," $Exp.$ $Eye$ $Res.,$ vol. 66, pp. 476–486 (1988). Various examples will be described below. Such examples serve to explain the principles of the invention and are not restrictive of the invention as claimed.

Materials

The following materials were used in the cloning, expression and characterization of human lens thioltransferase. pCR 3.1-Uri vector was purchased from Invitrogen. Primers for PCR amplification were custom made at Gibco-BRL. Expression vector pET-23a and its host cell BL2I (DE3) were obtained from Novagen Inc. T4 Poly nucleotide kinase, T4 DNA ligase, Taq DNA polymerase restriction enzymes, and random primer labeling kit were purchased from Gibco-BRL. Reagents for electrophoresis and immunoblots were purchased from Bio-Rad. Protein assay reagent was purchased from Pierce.

Construction of Human Lens cDNA Library

One hundred human lens capsulotomy specimens were obtained from Dr. Joseph Horwitz, Jules Stein Eye Institute, UCLA. Total RNA was extracted and mRNA was purified on an oligo dT column. The mRNAs were converted into cDNAs and the double stranded cDNAs were subcloned into Uni-Zap™XR vector using ZAP-cDNA synthesis Kit (Stratagene, La Jolla, Calif., U.S.A.) using EcoR 1 and XhoI 1 sites as described in the manual of the provider. The library was found to have $4 \times 10^6$ plaque forming units per µg original cDNA. The background of the library was less than 2%. Two microliters of the library was diluted (1:10) and used as the template for the PCR as described below.

Production of an Initial cDNA Clone by PCR

A 21mer sense (agcatggctcaagcatttgtg, SEQ ID NO:8) and a 24mer antisense (gaagaaaaatctgttttgtccccc, SEQ ID NO:9) primers were designed based on the known nucleotide sequence of pig liver thioltransferase (M31453 GenBank). The sense primer is phosphorylated by T4 Poly nucleotide kinase prior to amplification. This phosphorylated primer was used with the unphosphorylated antisense primer to generate a 520 bp PCR product phosphorylated on the 5' end using the template human lens cDNA library and Taq DNA polymerase. The conditions of the PCR in a reaction volume of 50 µL were as follows: 40 cycles at 94° C. for 1 min., 57° C. for 1.5 min. and 720° C. for 2 min. The PCR products were size fractionated on a 2% agarose gel and the band corresponding to 520 bp was separated and purified using Qiagen's Gel agarose purification Kit (Vogelstein et al., "Preparative and analytical purification of DNA from agarose," $Proc.$ $Natl.$ $Acad.$ $Sci.$ $U.S.A.,$ vol. 76, 615–79 (1979)). This purified PCR product was used for subsequent cloning purposes.

Cloning of Lens Thioltransferase into TA 3.1 Uni Vector

The purified PCR fragment was cloned downstream of CMV promoter into TA 3.1-Uni using T4 DNA ligase at 14° C. for 16 hr and Invitrogen's Top 10F cells were transformed with the recombinant pCR 3.1 Uni vector based on the method of Mead et al., "A universal method for the direct cloning of PCR amplified nucleic acid," *Bio/techno.,* vol. 9, pp.657–63 (1991)). The transformants were selected on LB plates with 50 μg/ml Kanamycin. The recombinant plasmid designated as PCR 3.1-HLTT were analyzed by restriction enzymes HindIII and EcoR1 for the presence of the insert.

Nucleotide Sequence Analysis of the Recombinant Lens Thioltransferase cDNA sequencing of the recombinant thioltransferase cDNA from both the 5' and 3' directions were performed on automated fluorescence DNA sequencer using Thermosequenase (Amersham) at the Licor-Biotech Inc., Lincoln, Nebr., U.S.A.

Sub Cloning into pET 23a Vector

PCR 3.1-HLTT was digested with Nhe1 and EcoR1 at 37° C. for 4 hr in React 4 buffer (Gibco). The HLTT cDNA fragment released after restriction enzyme digestion was separated on 2% agarose gel, purified and cloned into the Nhe1 and EcoR1 sites of pET 23a expression vector driven by T7 promoter using T4 DNA ligase. BL21 (DE3) cells were transformed with pET23a-HLTT and the transformants were selected on LB plates with 50 μg/ml ampicillin. The resulting positive clones were designated as pET23a-HLTT.

Expression of HLTT

Transformed BL21 cells were cultured at 37° C. in LB medium with 50 μg/ml ampicillin until an $OD_{600}$ of 0.4–0.6 was reached. At this time isopropyl thio galactoside (IPTG) was added to a final concentration of 0.5 mM and the culture was continuously incubated for up to 8 hr at 37° C. Equal number of cells (~1 ml) were removed at various time intervals (0, 2, 4, 6, 8 hr) to monitor the rate of HLTT induction.

Preparation of Crude Recombinant HLTT

Cells were harvested after 0, 2, 4, 6, and 8 hr of IPTG induction by centrifugation at 3500 g for 20 minutes and the pellet was resuspended in 1 ml of 10 mM phosphate buffer pH 7.4 containing 1 mM dithiothreitol (DTT). 1 mM phenyl methyl sulfonyl fluoride (PMSF), Lysozyme was added to a final concentration of 0.2 mg/ml with stirring and the cells were disrupted by sonication for 3 minutes at 30 second intervals. The lysed cells were centrifuged to remove the cell debris and the supernatant was used for protein analysis, thioltransferase assay, and Western blot analysis.

Protein Determination

Protein content of the crude extract was determined by the BCA protein assay protocol according to Smith et al., "Measurement of protein using BCA," *Anal. Biochem.,* vol. 150, 76–85 (1985), with bovine serum albumin as the standard.

Measurement of Thioltransferase Activity

Thioltransferase activity was measured as described previously (Raghavachari et al., "Evidence for the presence of thioltransferase in the lens," *Exp. Eye Res.,* vol. 63, 433–41 (1996)) with hydroxy ethyl disulfide (HEDS) as substrate. Briefly the reaction mixture contained 0.2 mM NADPH, 0.5 mM GSH, 0.1 mM Phosphate buffer, 0.4 units GSSG reductase and an aliquot of the crude cell extract. The reaction was initiated by the addition of 2 mM HEDS at room temperature and the decrease in absorbance at 340 nm was monitored in a Beckman spectrophotometer. A blank reaction without the enzyme was monitored simultaneously as a control blank.

Measurement of Dehydroascorbate Reductase Activity

Dehydroascorbate reductase activity was measured by the direct spectrophotometric method of Stahl et al., "A spectrophotometric assay for dehydroascorbate reductase," *Anal. Biochem.,* vol. 131, 341–44 (1983), based on the change in absorbance at 265.5 nm as dehydroascorbic acid is reduced to ascorbic acid. The reaction mixture contained 137 mM sodium phosphate buffer pH 6.8. 1 mM EDTA, 2 mM GSH, 1 mM DHA and various amounts of enzyme in a total volume of 500 μL. The reaction was initiated by the addition of DHA and the change in absorbance at 265 nm was monitored for 5 min. A blank without any enzyme served as the control.

Preparation of Protein Mixed Disulfides—PSSG and PSSC

Purified BSA, alpha and gamma crystallins from bovine lens were conjugated to $^3$H-GSH and $^{14}$C-cystine to form the corresponding protein-thiol mixed disulfides PSSG and PSSC based on the procedure of Dickerson et al., "The culture of rat lenses in high sugar media: effect on mixed disulfide levels," *Curr. Eye Res.,* vol.14, pp.109–18 (1994). In brief, to a 4 mg/ml of BSA, alpha and gamma crystallins were added 27.2 mg of 1 mci/ml $^3$H-GSH or 17.2 mg/ml $^{14}$C-cystine and the samples were maintained at 20° C. for 1 hr followed by a minimum of 18 hr at −20° C. The samples were then thawed and dialysed extensively to remove excess GSH, GSSG or cystine in 0.1 M potassium phosphate buffer pH 7 with 10 mM diethylene triamine penta acetic acid (DTPA). The purity of the synthesized protein-thiol mixed disulfides was verified on Superose 12 (gel filtration) column (Pharmacia) using Waters HPLC system. The incorporation of radioactivity in the mixed disulfide was determined simultaneously using the INUS β RAM system. The specific radioactivity of the synthesized BSA and crystallin-thiol mixed disulfides were found to be in the range of 0.25–0.7 Ci/Mol protein.

Dethiolation Assay with HLTT

Dethiolation of $^3$H or $^{14}$C labeled protein-thiol mixed disulfides was carried out with purified human lens thioltransferase by a procedure similar to Mannervik et al., "Role of cytoplasmic thioltransferase in cellular regulation by thiol-disulphide interchange," *Biochem. J.* vol. 190, pp. 125–30 (1980).

Initial specific radioactivities of all the radiolabeled substrates were within the range of 0.25–0.7 Ci/Mol protein. These substrates were incubated at 30° C. with 0.1 M potassium phosphate buffer pH 7.5, 2 units GSSG reductase, 0.2 mM NADPH, 0.5 mM GSH in the absence or presence of HLTT. After preincubation at 30° C. for 5 min., reactions were started by the addition of radiolabeled PSSG or PSSC to a final concentration of 2 mM. Reactions were terminated at various times by the addition of 1 volume of ice cold 20% TCA followed by centrifugation for 10 min. An aliquot of the supernatant was removed and added to 5 ml of bio-safe liquid scintillation cocktail and counted in the liquid scintillation counter. Net release of radioactivity in the supernatant per ml of the reaction mixture was calculated. Thioltransferase activity is then expressed as mol of PSSG or PSSC dethiolated per µg thioltransferase protein under the assay conditions mentioned above.

SDS-PAGE and Immunoblotting Analysis

The Laemmeli system (Laemmeli, "Cleavage of structural proteins during the assembly of the head of the bacteriophage T4," Nature, vol. 277, pp. 680–88 (1970)) was employed for SDS-PAGE analysis. Immunoblotting analysis was performed as described previously (Blake et al., "A rapid sensitive method for detection of alkaline phosphate conjugated antibody on western blots," Anal. Biochem., vol. 136, pp. 175–79 (1984)) in which polyclonal antiserum raised against PLTT was used as the primary antibody and alkaline phosphatase conjugated goat anti rabbit IgG color reaction system (BioRad) was used to detect the positive signals.

N-terminal Sequence Analysis

An aliquot of the crude recombinant HLTT after induction with IPTG was separated on 15% SDS-PAGE. The gel was transferred to PVDF (poly vinylidene difluoride) membrane and stained with amido black. The heavily stained band after 8 hr of IPTG induction corresponding to 11.5 KDa was sequenced on Procise-494sequencer at the Protein Core facility of University of Nebraska-Lincoln.

Northern Blot Analysis

Total RNA from bovine Lens, rabbit lens epithelial cells and pig liver were isolated and purified by the single step method of Chomczynski et al., "A single step method of RNA isolation by acid guanidium thiocyanate phenol-chloroform extraction," Anal. Biochem., vol. 162, 156–59 (1987). Approximately 10 µg of the total RNA extracted from bovine lens, rabbit lens epithelial cells, pig liver, humanplacenta, and 5 µg of 0.24–9.5 kilobase pair RNA ladder (Gibco-BRL) were electrophoresed on an 11×14 cm agarose formaldehyde gel. The gel was rinsed in DEPC water several times, and RNA was transferred to a Nytran membrane (Schleicher and Sehuell) using the Turboblotter rapid downward transfer system. The membrane was pre-hybridized and hybridized with human lens thioltransferase cDNA labeled with $^{32}$P at 65° C. for 1 hr. The membrane was washed for 15 min at room temperature in 2×SSC solution, 0.1% SDS twice. The final wash at high stringency was carried out at 60° C. for 15 min. The membrane was air dried and exposed to X-ray film for 2 days at −80° C. with intensifying screens. To determine the integrity and equal loading of RNA, duplicate samples along with RNA markers were ran simultaneously, stained with ethidium bromide and photographed.

Southern Blot Analysis

DNA from rabbit lens epithelial cell line were extracted by the method of Gross-Bellard et al., "Isolation of high molecular weight DNA from mammalian cells," Eur. J. Biochemistry, vol. 36, pp. 32–38 (1973). An aliquot of the genomic DNA was digested with EcoR1, HindIII, PvuII, Sac1, and fractionated by electrophoresis in 1% agarose gels. DNA was denatured and transferred to filters for hybridization analysis by Southern blotting (Southern, "Gel electrophoresis of restriction fragments," in Methods in Enzymology, (Wu, ed., 68, Academic Press: NY, (1979). The filters were hybridized with a $^{32}$PdCTP labeled human lens thioltransferase cDNA for 1 hr at 65° C. The membrane was processed as described earlier in Northern blot analysis and exposed to X-ray film.

Isolation, Purification and Cloning of Human Lens Thioltransferase cDNA

Amplification of HLTT from a pool of humans lens cDNA by PCR resulted in a single 520 bp fragment. This fragment was purified and cloned into pCR 3.1 Uni vector and pET 23a expression vector. The PCR fragment containing the entire coding sequence for HLTT was initially cloned into pCR 3.1 Uni vector. The recombinant clone was confirmed for the presence and orientation of the insert by restriction enzyme analysis with HindIII and EcoR1 and by DNA sequencing. To construct the pET expression system with HLTT, pCR 3.1-HLTT was digested with Nhe1 and EcoR1 to release a 540 bp fragment consisting of the entire coding sequence of HLTT and the released fragment was cloned into Nhe1 and EcoR1 sites of pET 23a expression vector. The resulting positive clones were further confirmed for the presence of the insert by DNA sequencing.

Our objectives to construct HLTT clones in two different vectors pCR 3.1 and pET 23a were (a), to obtain large amounts of the enzyme by over expression in E. coli using the pET vector and (b), to transfect a mammalian cell line using the pCR 3.1 Uni Vector. Restriction enzyme analysis and DNA sequence analysis clearly show that we have successfully made these recombinant clones which can now be used for future studies.

HLTT cDNA Sequence Analysis and Comparisons with Other Thioltransferases

The nucleotide and the deduced amino acid sequence of the coding region of the lens thioltransferase is shown in FIG. 1. The nucleotides are numbered from 5' to 3' and the amino acids are numbered from $NH_2$ to COOH termini. The sequence of the PCR primers used are underlined. The initiator methionine and the terminator signal are in bold. The 520 bp lens cDNA insert possessed a continuous open reading frame of 318 bp beginning with an ATG initiation codon and ending with a TAA termination codon followed by the 3'-noncoding region. The open reading frame encodes for a polypeptide of 106 amino acids starting with methionine and the predicted molecular weight of the encoded polypeptide is 11.784 KDa. On comparison with thioltransferases from other tissues using the GCG program, it was observed that the lens thioltransferase is 98% identical to that of the pig liver thioltransferase and has 87% similarity to that of the human placental glutaredoxin. FIG. 2 represents the alignment of the deduced amino acid sequence of lens thioltransferase to thioltransferases from other mammalian systems and E. coli. Sequence A is the human lens thioltransferase; sequence B is pig liver thioltransferase (Gan et al., "The primary structure of pig liver thioltransferase, J. Biol. Chem., vol.262, pp. 6699–6705 (1987)); Sequence C is human placenta (Padilla et al., "Purification from placenta, amino acid sequence, structure comparisons, and cDNA cloning of glutaredoxin, Eur. J. Biochem., vol.227,27–34 (1995)); sequence D is calf thymus thioltransferase (Klintrot et al., "The primary structure of calf thymus glutaredoxin. Homology with the corresponding E. coli protein but elongation at both ends with an additional half-cysteine/cysteine pair," Eur. J. Biochem.,vol. 144, pp.417–23 (1984)); sequence E is rabbit bone marrow (Hopper et al., "Glutaredoxin from rabbit bone marrow. Purification, characterization, and amino acid sequence determination by tandem mass spectroscopy," J. Biol. Chem., vol. 264, pp. 438–77 (1989); and sequence F is E. coli thioltransferase (Aslund et al., "Two additional glutaredoxins exist in E. coli: glutaredoxin is a hydrogen donor for ribonucleotide reductase in a thioredoxin/glutaredoxin double mutant," *Proc. Natl. Acad. Sci. U.S.A.,* vol. 91, pp. 9813–17 (1994)). The regions indicated by "*," "," and "*" are, respectively, the active site of the enzyme, residues in the hydrophobic region, and the GHS binding site. This alignment is based on the 3D structure of *E. coli* glutaredoxin (Aslund et al., supra) using the active site residues and structural elements in that molecule. As expected, the human lens thioltransferase has identical amino acid residues in the three highly conserved regions which are the active site of the enzyme. GSH binding site and the residues in the hydrophobic region as can be seen from FIG. 2. Similar to placental thioltransferase human lens thioltransferase has a cysteine residue in position 8 replacing serine in other thioltransferase. The only major difference between the lens thioltransferase and all other thioltransferase is the presence of valine in position 27 replacing arginine.

Over Expression of HLTT in BL21 Cells

Nhe1 and EcoR1 fragment of pCR 3.1-HLTT was subcloned into PET 23a expression vector. Positive clones designated as pET 23a-HLTT were further confirmed for the presence and orientation of the insert by sequence analysis. BL21 cells transformed with pET 23a-HLTT were then induced by 0.5 mM IPTG for 8 hr. There was a 65-fold increase in total activity of HLTT over the wild type *E. coli* after 8 hr of induction in the crude cell extract (data not shown). The HLTT protein band was also visualized at 11.5 KDa on 15% SDS-PAGE with the same cell extracts after staining with coomassie Blue R-250 (data not shown). This was verified by immunoblot analysis with anti pig liver thioltransferase along with the pig liver thioltransferase as positive control which showed a gradual increase in the intensity of the 11.5 KDa band, thus confirming the high level expression of a functionally active HLTT.

In addition, pure recombinant HLTT's intrinsic dehydro ascorbate reductase activity was found to be 7.8 nmoles/µg thioltransferase protein when measured with dehydro ascorbic acid as the substrate at 30° C.

Radiolabeled Dethiolation Assays

Alpha and gamma crystallin thiol mixed disulfides were chosen here as these are the lens proteins likely to form predominant disulfides with glutathione or cystine under oxidative stress and so can be considered as a well defined and convenient substrate for studying the catalysis of disulfide reduction. BSA-thiol mixed disulfides were used in comparison to determine the substrate preference of lens thioltransferase.

Figure 3B:
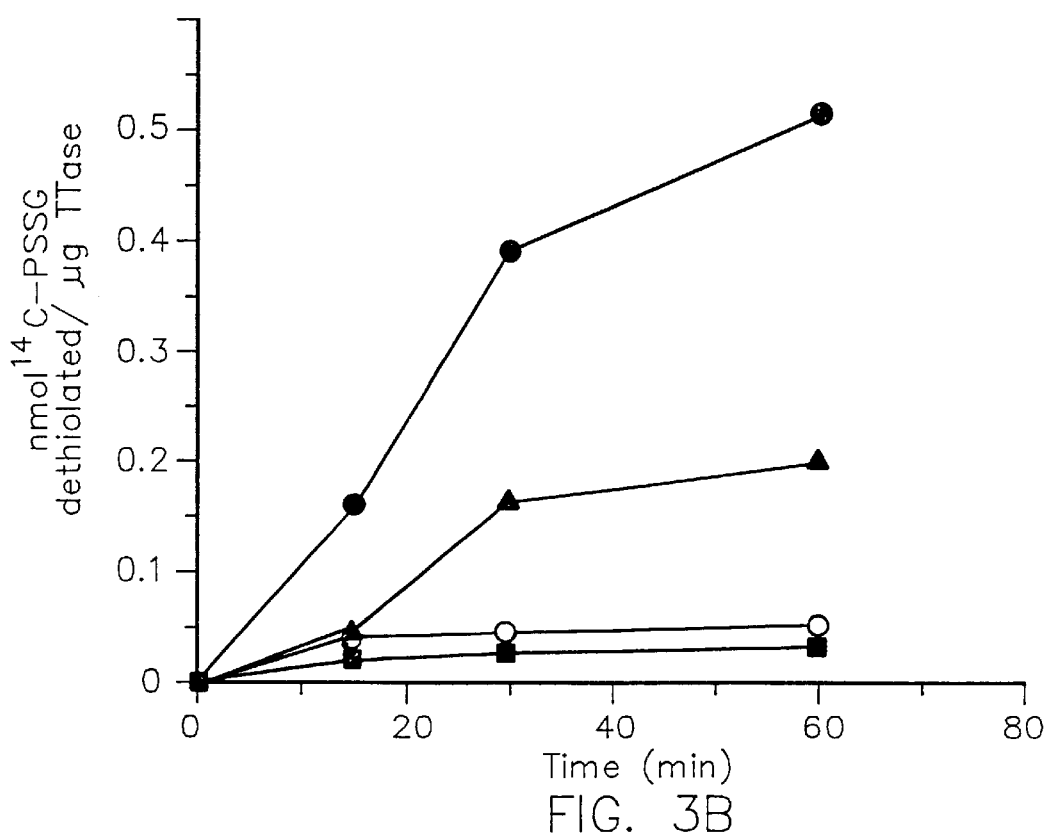

The rate of dethiolation was measured in terms of nmol of $^3$H-PSSG or nmol $^{14}$C-PSSC dethiolated per µg of thioltransferase protein. FIGS. 3A and 3B represent the time dependent dethiolation of PSSC and PSSC by lens thioltransferase. It can be seen from the slope of the reaction that the lens thioltransferase dethiolates gamma crystallin-GSH mixed disulfide more efficiently (1.15 nmol/µg thioltransferase), followed by alpha (0.6 nmol/µg thioltransferase) and BSA-GSH (0.3 nmol/µg thioltransferase) mixed disulfides. Due to the difference in the assay system these results were not compared to the spectrophotometric assay which measures the loss of NADPH at 340 nm coupled to GSSG formation while the radiolabel assay measures the TCA nonprecipitable counts.

The dethiolation of PSSC by lens thioltransferase was found to be lesser (50–60%) than with PSSG as can be seen from the FIGS. 3A and 3B, wherein -■- is control-thioltransferase; -●- is gamma crystallin mixed disulfide; -○- is alpha crystallin mixed disulfide; and -▲- is BSA mixed disulfide. FIG. 3A shows the dethiolation of alpha, gamma crystallins and BSA-GSH mixed disulfides (PSSG). FIG. 3B shows the dethiolation of alpha, gamma crystallins and BSA-Cystine mixed disulfides (PSSC). Interestingly, alpha crystalline-cystine mixed disulfide could not be dethiolated by lens thioltransferase Gamma crystallin-thiol mixed disulfide appears to be the favorable substrate for lens thioltransferase.

N-terminal Amino Acid Analysis of the Human Lens Thioltransferase

The N-terminal amino acid sequence analysis indicated the first 10 amino acids of the expressed enzyme to be AQEFVNCKIQ (amino acids 2–11 of SEQ ID NO:2) which is in agreement with that of the deduced amino acid sequence of the protein from the cDNA (FIG. 1). Methionine which precedes alanine as deduced from the cDNA sequence was not found at the N terminus of the expressed recombinant protein indicating its likely cleavage by the host cell. The expressed product, similar to other reports, did not show any acetyl group at the N-termini.

Northern Blot Analysis

In order to determine the size of the mRNA transcript of lens thioltransferase, total RNA from bovine lens, pig lens, rabbit lens epithelial cell, pig liver, and human placenta (as positive control) were hybridized to the human lens thioltransferase cDNA labeled with $^{32}$P. The results showed the presence of a single positive band with an approximate size of 0.8 kb (not shown). This also confirmed the sequence homology of lens thioltransferase to that of liver and placental thioltransferase.

Southern Blot Analysis

Genomic DNA digested with EcoR1, HindIII, PvuII, and SacI were examined by Southern hybridization using human lens thioltransferase cDNA as probe. Digestion with EcoR1 and HindIII showed a single positive signal upon hybridization with $^{32}$P labeled human lens thioltransferase cDNA. SacI which has 3 restriction sites resulted in 4 fragments which hybridized with the HLTT cDNA while PvuII digestion resulted in 2 positive signals. These results suggest that the thioltransferase gene is a single copy gene.

The above described cloning and sequencing of the human lens thioltransferase is advantageous in that we have been able to produce large amounts of the enzyme, which would not otherwise be possible due to the low concentration of the enzyme in the lens and the difficulty in obtaining the human lens tissue. The recombinant protein that we have now obtained has been characterized by SDS-PAGE, Immunoblots and N-terminal amino acid sequencing and our results clearly demonstrate the structural similarity of HLTT to that of thioltransferases from other mammalian systems. Southern and Northern hybridizations provide strong evidence for the presence of a single copy gene for thioltransferase and the mRNA transcript size has been found to be approximately 0.8 kb.

The findings above show the dethiolation of PSSG and PSSC by lens thioltransferase and its intrinsic dehyrdoascorbate reductase activity to regenerate ascorbic acid from its oxidized form indicate that the antioxidant role of thioltransferase is both as a protective agent against oxidation by its ability to regenerate ascorbic acid and as a repair enzyme by its dethiolating activity, thus preventing protein aggregation, an earlier event in cataractogenesis.

The amino acid sequence of HLTT as expected was found to be similar to a large extent to that of other thioltransferases. This similarity involves all residues previously known to be highly conserved based on the 3-dimensional structure of *E. coli* glutaredoxin or thioltransferase (Aslund et al., supra), the active site with 2 half cystine residues cys-pro-tyr-cys (amino acids 11–14 of SEQ ID NO:7) is conserved in HLTT similar to other thioltransferases. In addition, as shown in FIG. 2, there are 2 other highly conserved areas outside the active site in all the thioltransferases, including HLTT. These include the residues thr-val-pro, representing the hydrophobic surface area in *E. coli* grx and the residues ile-gly-gly-cys-ser (amino acids 80–84 of SEQ ID NOS:4 and 6) or ile-gly-gly-thr-asp (amino acids 69–73 of SEQ ID NO:7) representing the GSH binding site in *E. coli*. Another interesting observation is the presence of cysteine in position 8 (a non conserved region) and 79 (conserved region for human thioltransferases). It has been speculated that these 2 residues in conjunction with the GSH binding site and the site of the enzyme constitute a redox regulatory part of the enzyme (Padilla et al., supra). As seen in FIG. 2 showing the alignment of amino acid residues in thioltransferases, all thioltransferases exhibit a high degree of similarity, indicating a highly conserved structure. The human lens thioltransferase on the whole has 5 cysteine residues similar to human placental thioltransferase, an internal methionine and histidine in contrast to human placental thioltransferase, which does not have these residues and there are no tryptophan residues as reported by Mieyal et al., *Biochemistry*, vol. 30, 6088–97 (1991), in the RBC thioltransferase. Cystine 8 is a replacement of serine in human lens thioltransferase similar to te report of Padilla et al., supra, on human placental thioltransferase. Another interesting observation is the replacement of arginine with valine in HLTT in position 27 immediately following the active site.

Also contemplated as within the scope of the present invention is the use of an HLTT clone such as the pCR3.1-HLTT clone as described herein transfect mammalian cell lines, and the cell lines so transfected. Such transfected cell lines are useful in that they can be used to evaluate the effect of thioltransferase on lens proteins subjected to oxidative stress. Also contemplated as within the scope of the invention are antisense polynucleotides and a method for causing thioltransferase depletion in a cell by the introduction of an antisense molecule. Such an antisense molecule may be an RNA or a single stranded DNA that is complimentary to the mRNA of the HLTT gene to prevent translation of the HLTT protein. Such antisense molecules are useful evaluating the effect of thioltransferase depletion. The creation and comparison of cell lines which over and under express thioltransferase would also be useful in providing an excellent model for the study of the cellular functions of oxidative stress in general, and cataractogenesis in particular.

The following Examples demonstrate that, under oxidative stress induced by $H_2O_2$ exposure, thioltransferase shows remarkable resistance to oxidation, while other defense enzymes, such as glutathione peroxidase and glutathione reductase, exhibit a transient loss of activity.

Materials

Rabbit lens epithelial cell lines, N/N 1003 A and OB3L were established in Dr. John Reddan's laboratory at Oakland University, Rochester, Mich. MEM, rabbit serum, trypsin-EDTA (1x) and gentamicin solution, glutathione, glutathione reductase, glutathione sulfonic acid, cysteic acid and $H_2O_2$ were from Sigma Chemical Company (St. Louis, Mo.). Hydroxyethyl disulfide (HEDS) was purchased from Aldrich Chemical Company (Milwaukee, Wis.). The BCA protein assay kit was from Pierce Chemical Company (Rockford, Ill.). Nylon membrane and nitrocellulose membrane were from Schleicher and Schuell (Keene, N.H.). Ethidium bromide was purchased from Boehringer Mannheim Corp. (Indianapolis, Ind.). All other chemicals and reagents were of analytical grade.

Rabbit Lens Epithelial Cell Culture

Rabbit lens epithelial cell line N/N1003 A was developed from a four-day-old rabbit (Reddan et al., "Establishment of epithelial cell lines from individual rabbit lenses," *J. Tissue Culture Methods*, vol. 6, 57–60 (1980); Reddan et al., "Retention of lens specificity in long-term cultures of diploid rabbit lens epithelial cells," *Differentiation*, vol.33, 168–174 (1986)) and OB3L was from an eight-year-old rabbit ( Reddan et al., "Establishment and characterization of a lens epithelial cell line from an 8-year old rabbit," *Curr. Eye Res.*, vol. 2, 633–639 (1983)). Cells were grown in 5 ml of MEM with 50 µg/ml gentamicin plus 8% rabbit serum (pH 7.2) in 60×15 mm tissue culture plates in a humidified atmosphere with 5% $CO_2$ at 35.5° C. Cells reached 95% confluence (~2×10$^6$ cells) within 3–4 days. They were divided four to one with fresh medium and subcultured.

$H_2O_2$ Treatment of Lens Epithelial Cells in Culture

Rabbit lens epithelial cells were raised to confluence, trypsinized and plated at 0.8 million in each dish. The cells were incubated overnight in MEM with 1% rabbit serum and then in serum free MEM for 30 min before a bolus of 0.5 mM $H_2O_2$ was added. Serum-free medium was used to minimize reaction of peroxide with serum proteins. At intervals of 5, 15, 30 min and up to 3 hours, cells in quadruplicate plates were harvested and used for various enzymatic assays (TTase, GR, GPx and G-3PD). Free GSH, total SH and protein-thiol mixed disulfides (PSSG and PSSC) were determined. $H_2O_2$ in the medium was measured at each time point. A portion of the cells was saved for a DNA fragmentation assay. Other cells were photographed and tested for viability by Trypan Blue staining. Cells were also exposed to different levels of $H_2O_2$ (0.5–1.0 mM) to study the resistance of thioltransferase to $H_2O_2$ stress. In each study, cells incubated without $H_2O_2$ were used as controls.

Harvest of Cells and Preparation of Cell Homogenate

The cells in each plate were harvested by scraping with a rubber policeman and the suspension was centrifuged at 1,700×g for 15 min at 4° C. The pellet was resuspended in 5 ml, 2 mM EDTA, sonicated to break the cells and centrifuged to collect the supernatant, which was either used immediately or stored at −20° C. for biochemical assays. Protein content in the homogenate was determined using a Pierce BCA kit, following the method of Smith et al., "Measurement of protein using BCA," *Anal. Biochem.*, vol.150, 76–85 (1985).

Quantification of Total Thiols, GSH and Protein-Thiol Mixed Disulfides

A portion of the cell homogenate was centrifuged and the supernatant was immediately used for total thiol assay (GSH plus Protein thiol) following the method of Ellman, "A colorimetric method for determining low concentrations of mercaptans," *Arch. Biochem. Biophys.,* vol.74, 443–50 (1958). Another portion of the homogenate was treated with an equal volume of 20% TCA, centrifuged and the supernatant was immediately assayed for GSH with Ellman's reagent (expressed as nmoles/mg protein). The TCA precipitate was used for quantification of PSSG and PSSC following the method of Lou et al., "Protein-thiol mixed disulfides in human lens," *Exp. Eye Res.,* 55, 889–96 (1992). Briefly, the TCA precipitate was washed thoroughly (3×) with 10% TCA followed by a wash with ether/methanol (1/1, v/v) and dried in a dry heating bath (65° C.) overnight. The dried protein was pulverized and then oxidized with performic acid to release non-protein thiols from lens proteins. The released products of GSH (as glutathione sulfonic acid), and cysteine (as cysteic acid) were quantified by anion exchange amino acid analysis using a Dionex LC system (Sunnyvale, Calif.). Values were expressed as nmoles/mg dry weight.

Enzyme Assays of the Cell Homogenate

In each enzyme assay, reaction mixtures without the cell homogenate were used as blanks. The activity of each enzyme was expressed as miniunit (mU)/mg protein. Thioltransferase was assayed following the method of Mieyal et al., supra, as modified by Raghavachari et al., "Evidence for the presence of thioltransferase in the lens," *Exp. Eye Res.,* vol. 63, 433–41 (1996). The reaction was carried out in the presence of NADPH, GSH and GR with the synthetic disulfide, hydroxy ethyl disulfide (HEDS), as substrate. The decreased O.D.$_{340nm}$ for NADPH was monitored for enzyme activity. GPx was assayed following the method described by Spector et al., "The prevention of cataract caused by oxidative stress in cultured rat lenses. I.$H_2O_2$ and photochemically induced cataract," *Curr. Eye Res.,* vol.12, 163–179 (1993), based on the decreased absorption at 366 nm as the result of GPx catalyzed oxidation of NADPH by substrate $H_2O_2$. GSH and GR were added as cofactors. The GR assay was performed following the method of Straatsma et al., "Lens capsule and epithelium in age-related cataract," *Am. J. Ophthalmol.,* vol. 112,283–96(1991), using GSSG as substrate. The decreased absorbance (340 nm) with NADPH consumption was monitored for GR activity. G-3PD activity was determined using the method of Byers, "Glyceraldehyde-3-phosphate dehydrogenase from yeast," *Methods Enzymol.,* vol.89, 327–35 (1982), modified by Spector et al. (1993), supra. The reaction was initiated by addition of glyceraldehyde-3-phosphate and the change in absorbance at 340 nm between 20–50 second was used to determine G-3PD activity.

$H_2O_2$ Measurement in the Culture Medium

The concentration of $H_2O_2$ was measured using a colorimetric method of Hildebrandt et al., "Hydrogen peroxide in hepatic microsomes," *Meth. Enzymol.,* vol. LII, 342–350 (1978), modified by Spector et al. (1993), supra. An aliquot of the medium (50 μL) was mixed thoroughly with 950 μL of autoclaved, double-distilled water containing 50 μL of 50% TCA, followed by mixing with 50 μL of 30 mM ferroammonium sulfate and 50 μL of 2.5 M KSCN. The absorbance was read at 480 nm after standing at room temperature for 10–15 min. A standard curve of $H_2O_2$ with known concentrations was generated for calculation.

Assay for DNA Fragmentations in the Epithelial Cells

DNA fragmentation analyses followed the procedures of Hogquist et al., "Interleukin which is processed and released during apoptosis," *Proc. Natl. Acad. Sci. U.S.A.,* vol. 88, 8485–8490 (1991), and Prigent et al., "A safe and rapid method for analysing apoptosis-induced fragmentation of DNA extracted from tissues or cultured cells," *J. Immunol. Methods,* vol. 160, 139–140 (1993). This method is used to analyze apoptosis-induced fragmentation of DNA. Approximately 5×10$^6$ cells were washed in serum-free medium and centrifuged to collect the cell pellet. DNA was then isolated and treated with RNase to remove RNA before separating by agarose gel electrophoresis (2%). DNA was stained by ethidium bromide and photographed under UV illumination.

Effect of $H_2O_2$ on the Growth of Lens Epithelial Cells

Three rabbit epithelial cell lines N/N 1003A and OB3L were each seeded at 5×10$^4$ per plate containing 5 ml MEM plus 1% rabbit serum. Cells cultured in MEM with 1% rabbit serum remain viable but do not grow. Three plates from each line were counted 20 hours later to verify the starting count. Cells from the remaining plates were cultured for 30 minutes in serum-free MEM and then in medium containing a single dose of 0.05 mM $H_2O_2$. After 3 hrs, the medium was replaced with MEM containing 8% rabbit serum. The serum-containing medium was replaced on days three and six and cells were counted on day seven using a Coulter Counter (Miami, Fla.).

Effect of a Single Bolus of $H_2O_2$ on Lens Cells

Figure 4:
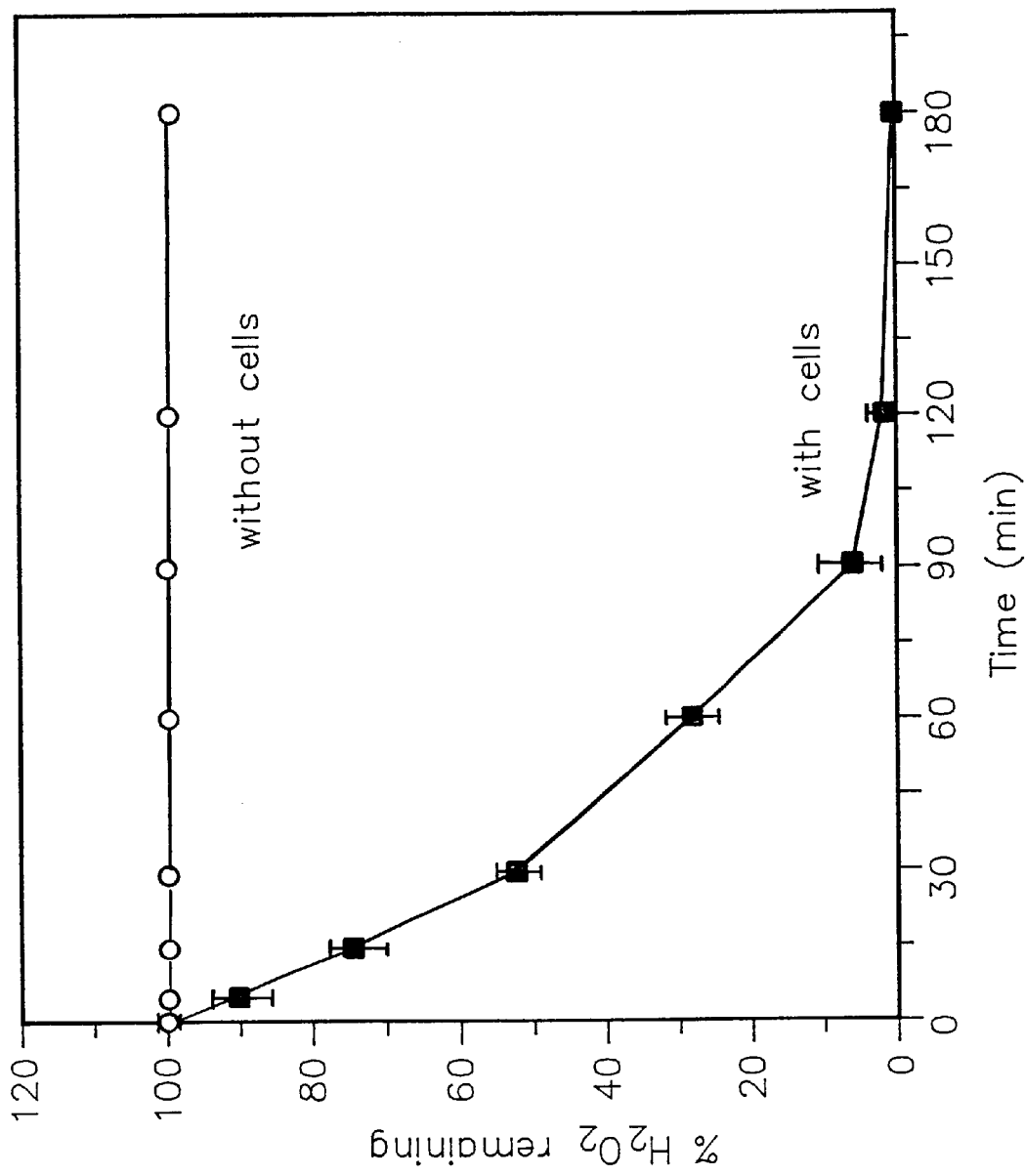
FIG. 4 shows the detoxification of bolus $H_2O_2$ (0.5 mM) by rabbit lens epithelial cell line N/N 1003A.

A single dose of $H_2O_2$ (0.5 mM) in the medium was degraded quite rapidly when incubated in the presence of 800,000 lens epithelial cells. FIG. 4 depicts the detoxification of bolus $H_2O_2$ (0.5 mM) by rabbit lens epithelial cell line N/N1003A in the absence of lens cells (-○-) and in the presence of lens cells (-■-). The level of $H_2O_2$ in the medium decreased with time. Half of the $H_2O_2$ was detoxified after 30 min and it was completely dissipated within 120 min. In contrast, the level of $H_2O_2$ remained constant when added to MEM and incubated without cells. The morphology of the $H_2O_2$-treated N/N1003A cells was identical to controls during the 3 hr exposure. Trypan Blue staining confirmed that the cells exhibited little or no cell death (data not shown). DNA fragmentation assay (data not shown) showed that these cells exhibited no DNA damage, strongly confirming the absence of apoptosis.

Figure 5:
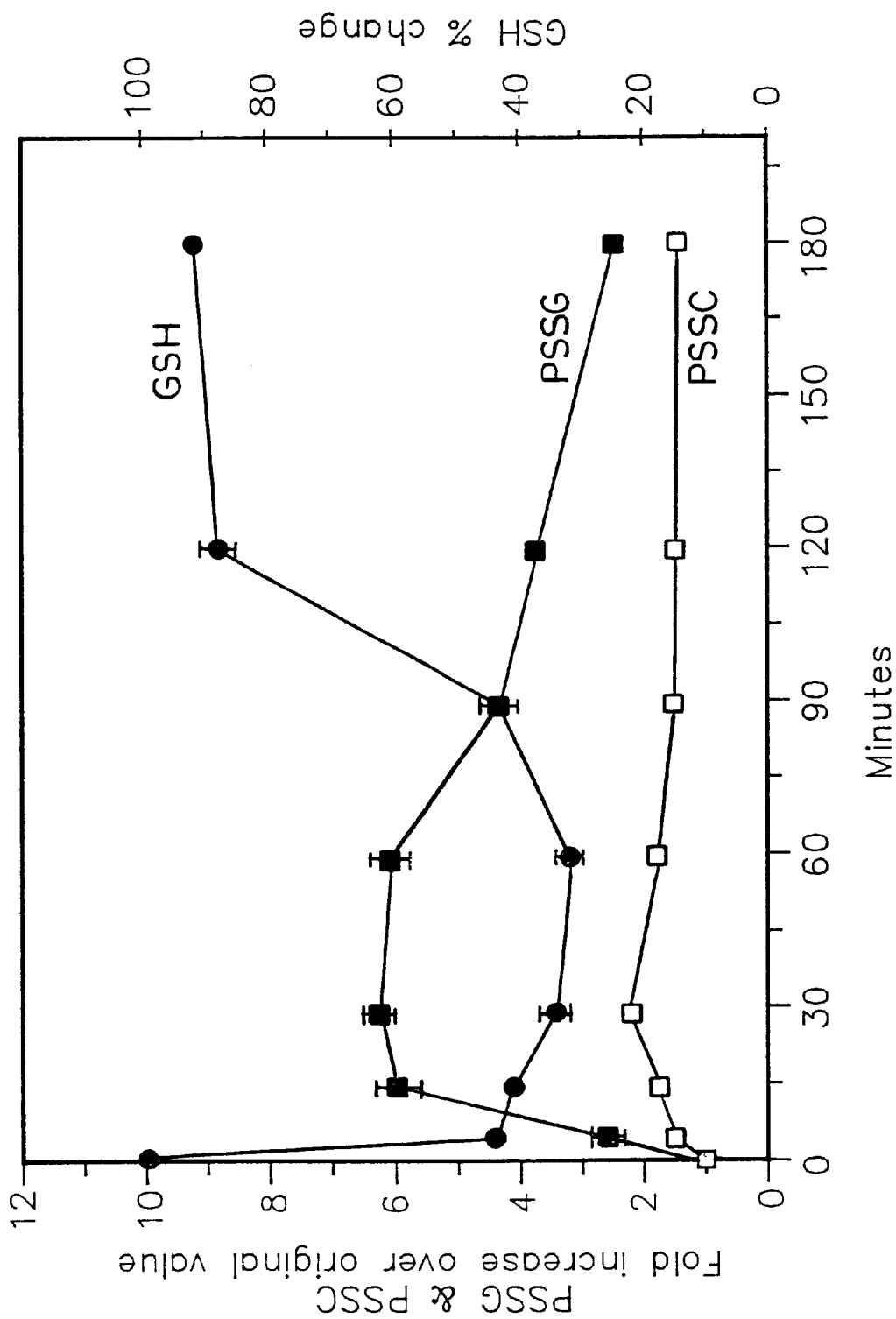
FIG. 5 shows the effect of bolus $H_2O_2$ to lens GSH and protein-thiol mixed disulfide in N/N 1003A cells.

Effect of Bolus $H_2O_2$ Treatment on Lens SH and Protein-Thiol Mixed Disulfides Following treatment with 0.5 mM $H_2O_2$ the cellular GSH level dropped 60% from 68.7±14.9 nmoles/mg protein within five min and stayed at this level before it began to increase at 90 min and recovered to nearly 100% of normal by two hrs (FIG. 5). FIG. 5 shows the effect of bolus $H_2O_2$ to lens GSH and protein-thiol mixed disulfide in N/N 1003A cells wherein GSH level is represented by -●-, PSSG level, measured as GSO3H, is represented by -■-, PSSC level, measured as CSO3H, is represented by -□-. The initial GSH concentration was 68.7±14.9 nmoles/mg; PSSG was 0.19±0.02 nmoles/mg dry wt (n=4); PSSC was 0.07±0.01 nmoles/mg dry wt. The total SH groups (GSH plus protein SH) showed a similar pattern to free GSH in response to $H_2O_2$ (data not shown). In contrast to the decrease in GSH, protein-thiol mixed disulfides were greatly increased. As shown in FIG. 5, PSSG was elevated 6.5 fold over the basal level of 0.07±0.01 nmoles/mg dry wt and reached a plateau within 15 minutes. The increase in protein-thiol mixed disulfides was inversely related to the level of GSH in the cells. The level of protein-thiol mixed disulfides began to decline only after the level of free GSH increased. At this time $H_2O_2$ in the medium was almost completely detoxified (90 min). The PSSG level continued to decrease at intervals beyond 60 min (see FIG. 5). Similar to PSSG but in much smaller scale, the level of PSSC also peaked (2-fold increase from a basal level of 0.19±0.02 nmoles/mg dry wt) 30 min after $H_2O_2$ was added and then decreased to the basal level at 90 min.

Effect of a Bolus of $H_2O_2$ on Enzymes in Lens Epithelial Cells

Figure 6:
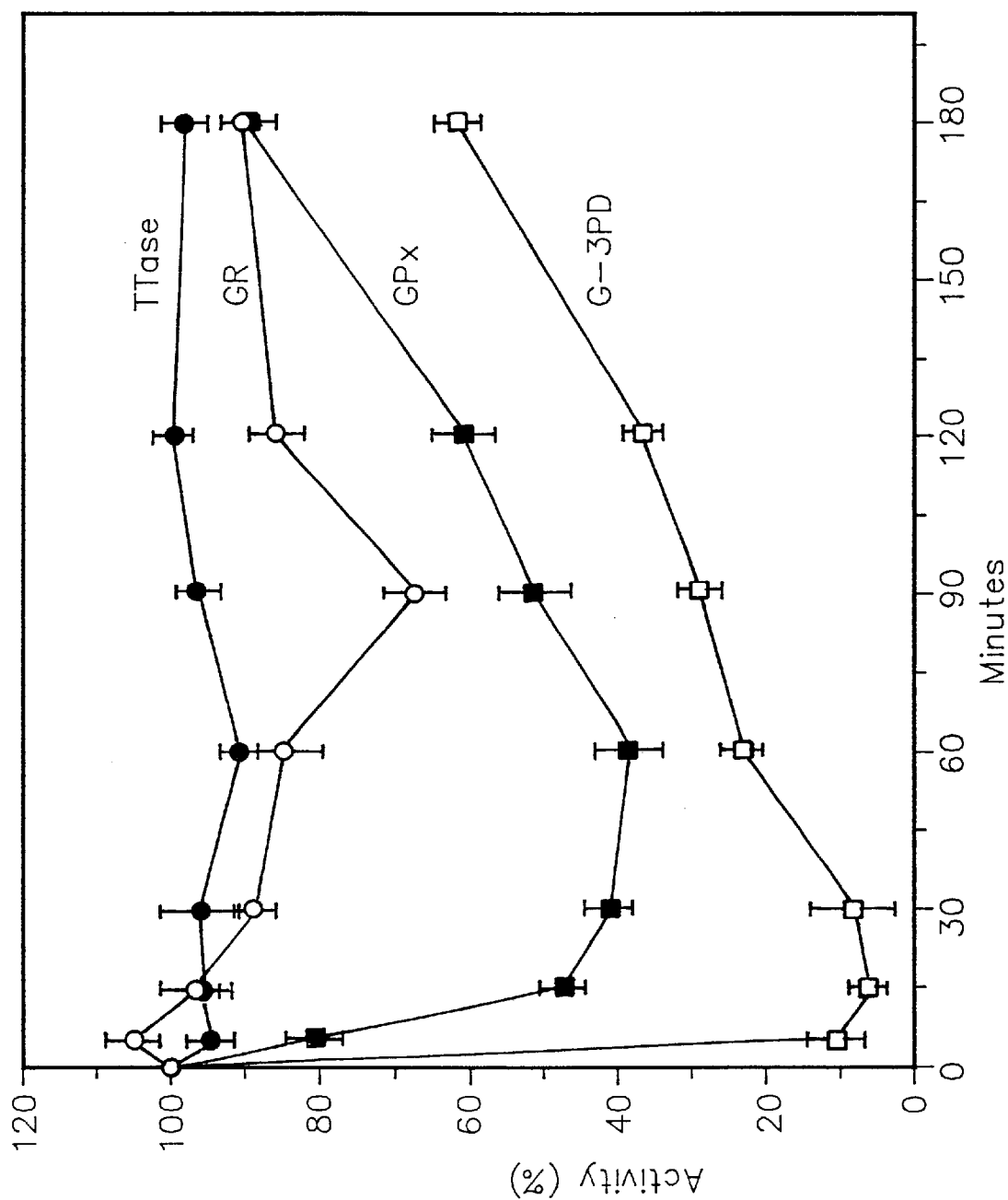
FIG. 6 shows the effect of bolus $H_2O_2$ (0.5 mM) on enzyme activities in N/N1003A cells.
Figure 7:
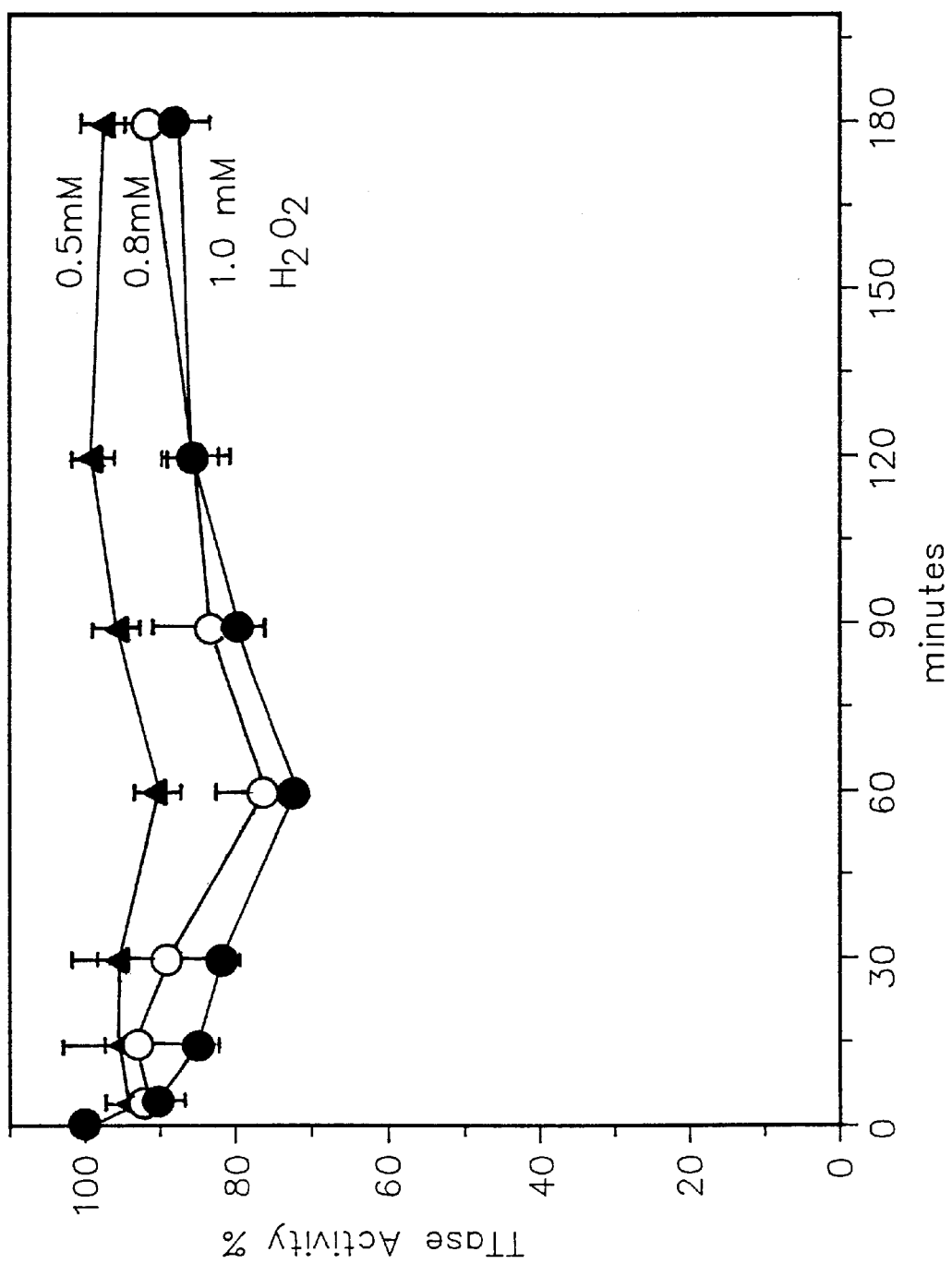
FIG. 7 shows thioltransferase activity in lens epithelial cells (N/N 1003A) treated with various levels of $H_2O_2$.

Since this study is focused on the response of thioltransferase to $H_2O_2$, it was considered important to compare the effect of $H_2O_2$ on the activity of thioltransferase with its effect on other enzymes. FIG. 6 shows the effect of bolus $H_2O_2$ (0.5 mM) on enzyme activities in N/N1003A cells wherein -●- represents thioltransferase; -□- represents glycero-3-phosphate dehydrogenase; -■- represents glutathione peroxidase; and -○- represents glutathione reductase. The initial thioltransferase activity was 16.0±5.6 mU/mg (n=24); G-3PD was 167±5.5 mU/mg (n=4); GPx was 19.1±4.3 mU/mg (n=4); GR was 26.4±1.8 mU/mg (n8). The data is expressed as mean±S.D. As shown in FIG. 6, glycero-3-phosphate dehydrogenase (G-3PD) was the most sensitive to $H_2O_2$ of the enzymes tested. It lost 95% of its activity from the initial value of 167±5.5 mU/mg within 5 min of $H_2O_2$ treatment. The activity was regained quickly when $H_2O_2$ began to diminish in the medium. When $H_2O_2$ was no longer present in the medium (120 min), G-3PD regained 40% of its activity and recovered up to 60% of the activity after 180 min. A less severe and delayed inhibition was observed in the activity of both GPx (60% maxima loss at 60 min from 19.1±4.3 mU/mg) and GR (30% maxima loss at 90 min from 26.4±1.8 mU/mg). In marked contrast, thioltransferase activity remained constant during the entire experiment (at 16±5.6 mU/mg, see FIG. 6). Only when a higher dose of $H_2O_2$ (0.8–1.0 mM) was used, did thioltransferase show a brief loss in activity (<30% maximum at 60 min) and a swift recovery (FIG. 7). FIG. 7 shows thioltransferase activity in lens epithelial cells (N/N 1003A) treated with various $H_2O_2$ levels wherein -Δ- represents 0.5 mM $H_2O2$; -○- represents 0.8 mM $H_2O_2$; and -●- represents 1.0 mM $H_2O_2$. The initial thioltransferase activity was 16.0±5.6 mU/mg (n=24).

One other line of rabbit lens epithelial cells was tested for its response to $H_2O_2$. OB3L, which originated from an eight-year old rabbit, showed similar pattern in thioltransferase, GSH and G-3PD activity as line N/N1003A (FIG. 6) after $H_2O_2$ treatment (data not shown).

Effect of $H_2O_2$ on the Growth of Rabbit Lens Epithelial Cells

Figure 8:
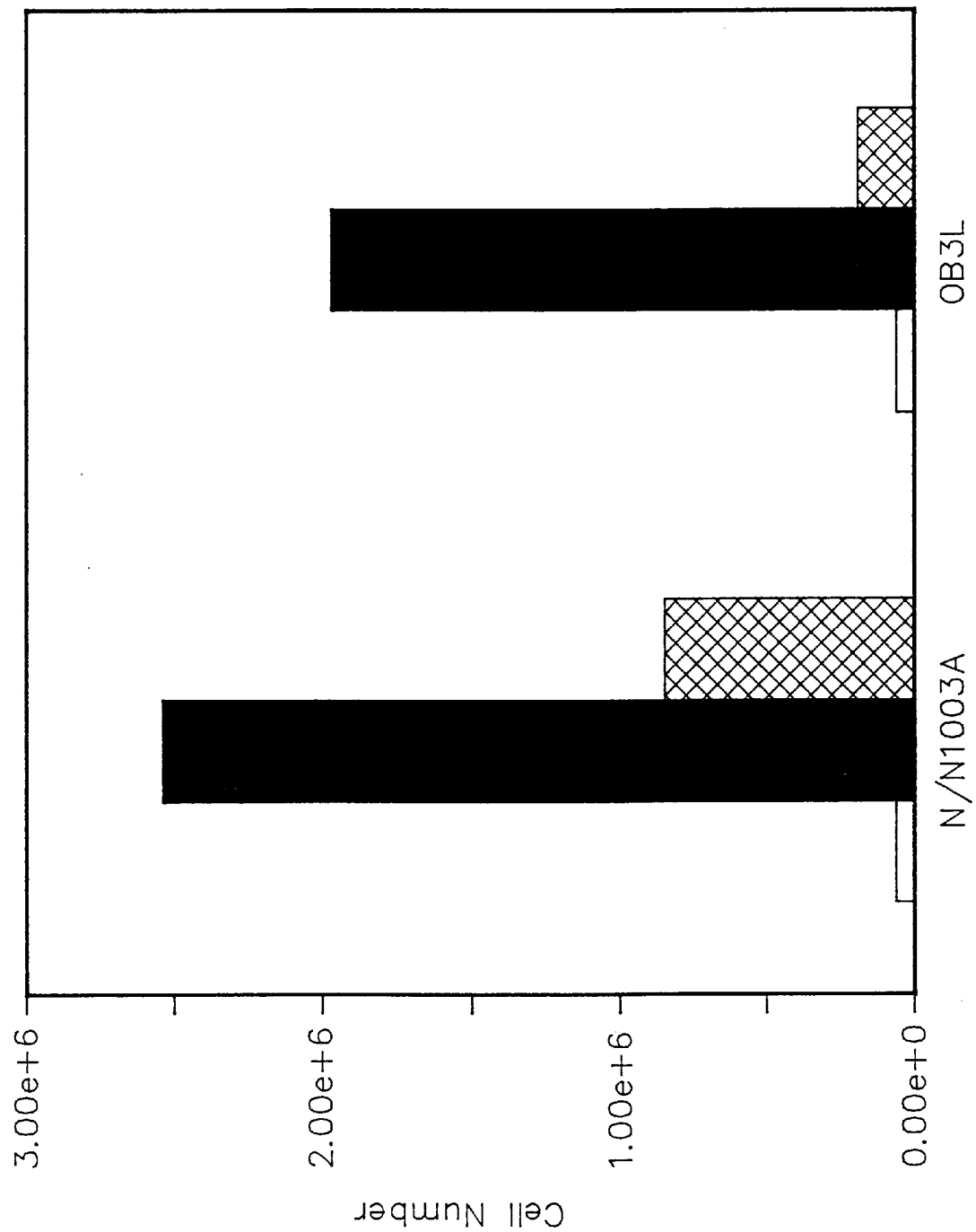
FIG. 8 shows the effect of $H_2O_2$ on the growth of rabbit lens epithelial cells.

Since proliferation is a sensitive indicator of oxidative damage we examined the effect of a single dose of 0.05 mM $H_2O_2$ on the growth of 50,000 cells from each of the cell lines. Controls were not treated with $H_2O_2$. Cells (50,000) in serum-free MEM were exposed to 0.05 mM $H_2O_2$. Three hours after $H_2O_2$ addition, cells were cultured in MEM containing 8% rabbit serum, a medium known to foster cell proliferation. Cells were counted 7 days after $H_2O_2$ treatment. The cells that were not exposed to $H_2O_2$ increased to 2–2.5 million cells in seven days. The susceptibility of the two cell lines to $H_2O_2$-induced growth inhibition varied. Cell line N/N 1003A was more resistant to oxidation and grew from 50,000 to 830,000 cells, a 16-fold increase over the inoculum. Cells from line OB3L increased to 180,000, a 3.6 fold increase in number. These results are summarized in FIG. 8 wherein □ represents the starting count, ● represents the control, and ⊠ represents the $H_2O_2$ treated cells.

Rabbit lens epithelial cell line N/N1003A was chosen since it has a high level of antioxidant enzymes (Giblin et al., "Detoxification of $H_2O_2$ by cultured rabbit lens epithelial cells: Participation of the glutathione redox cycle," *Exp. Eye Res.*, vol. 40, 827–40 (1985); Giblin et al., "The relative roles of the glutathione redox cycle and catalase in the detoxification of $H_2O_2$ by cultured rabbit lens epithelial cells," *Exp. Eye Res.*, vol. 50, 795–804 (1990)). This study focused on thioltransferase, an enzyme that has not been previously studied in cultured lens epithelial cells. The protocol for the present study of oxidative-stress induced by a bolus of $H_2O_2$ was similar to that of Giblin et al., 1990, supra. The rate of $H_2O_2$ dissipation in this study agrees with the earlier report (Giblin et al., 1990, supra). $H_2O_2$ in the medium was removed very efficiently by the lens cells from the two rabbit cell lines, indicating that these cells can defend themselves against this level of oxidative insult. Cells from line N/N1003A subjected to a bolus of $H_2O_2$ exhibited a normal morphology without visible DNA fragmentation. The fact that there was no DNA fragmentation is consistent with the viability and growth data and indicates that the cells exposed to $H_2O_2$ did not undergo apoptosis. It should be noted however, that $H_2O_2$ does induce single strand breaks in DNA following exposure of lens epithelial cells to $H_2O_2$ (Spector et al., "Repair of $H_2O_2$-induced DNA damage in bovine lens epithelial cell cultures," *Exp. Eye Res.*, vol. 49,685–698 (1989); Reddan et al., "The superoxide dismutase mimic TEMPOL protects cultured rabbit lens epithelial cells from hydrogen peroxide insult," *Exp. Eye Res.*, vol.56,543–554 (1993)). N/N1003A showed a stronger resistance to $H_2O_2$ induced mitotic inhibition (see FIG. 8) compared to cells from the other cell line, OB3L. One of the factors that may contribute to the increased susceptibility of line OB3L to $H_2O_2$ insult is that these cells have a lower level of GR than line N/N1003A (Reddan et al., "Influence of the activity of glutathione reductase on the response of cultured lens epithelial cells from young and old rabbits to hydrogen peroxide," *Exp. Eye Res.*, vol. 45, 209–221 (1988)).

The redox status of the cells changed with the amount of $H_2O_2$ present in the medium. At the initial burst of oxidation, GSH immediately decreased, likely due to its swift usage for various defense enzymes to combat the stress. The oxidized GSH quickly formed protein-GSH mixed disulfide, as can be seen in FIG. 5 where a mirror image of these two parameters is shown. The total thiols in the cells also decreased during this period, reflecting the general change in the redox status, i.e., sulfhydryl groups in GSH and proteins were oxidized with the concomitant formation of protein-thiol mixed disulfides. GSH levels began to recover as $H_2O_2$ in the medium diminished. Moreover, as the intracellular level of GSH increased, the accumulated PSSG in the cell decreased. This finding agrees with the lens organ culture studies where elevated PSSG was spontaneously dethiolated over a period of time after the $H_2O_2$ exposed lens was cultured in peroxide-free medium (Cui et al., "The effect and recovery of long term $H_2O_2$ exposure on lens morphology and biochemistry," *Exp. Eye. Res.*, vol. 57, 157–167 (1993); Lou et al., "Recovery of oxidative damage in human lenses," *Invest. Ophthalmol. Vis. Sci.* vol. 35 (Suppl.), 1569 (1994); Lou et al., "Further studies on the dynamic changes of glutathione and protein-thiol mixed disulfides in $H_2O_2$ induced cataract in rat lenses: distributions and effect of aging, *Curr. Eye Res.*, vol. 14,951–958 (1995); Wang et al., "Relationship of protein-glutathione mixed disulfide and thioltransferase in $H_2O_2$-induced cataract in cultured pig lens," *Exp Eye Res.*, vol. 64, 693–700 (1997)). In the organ culture study, we speculated that an enzyme must be present in the lens to dethiolate the glutathione thiolated protein (PSSG). This may also apply to the lens epithelial cells. Our recent discovery of the dethiolating enzyme, thioltransferase, in the lens and the presence of mRNA in the cultured lens epithelial cells (Wu et al., Distribution of thioltransferase in ocular tissues," *Invest. Ophthalmol. Vis. Sci.*, vol. 39, 476–80 (1998)) strongly supports such a hypothesis.

Of all the enzymes tested in this study thioltransferase was the only one whose activity was not adversely affected by $H_2O_2$. This oxidative stress-resistant nature was uniform in both rabbit lens cell lines. Thioltransferase activity was only slightly reduced when cells from line N/N1003A were exposed to a bolus of 0.8–1.0 mM $H_2O_2$ (FIG. 7). G-3PD was extremely sensitive to oxidation, which agrees with the observation of Jedziniak, "Photo-oxidative damage to lenticular GAPDH and its relationship to aldehyde metabolism," *Exp. Eye Res.*, vol. 50, 589–596 (1990). The phenomenon of a near-total loss in activity at the onset of $H_2O_2$ insult and a slow recovery in activity of this enzyme was noted in the present study. Two known oxidation-defense enzymes, GR and GPx showed a substantial loss of activity before they were restored.

Axelsson et al., "An essential role of cytosolic thioltransferase in protection of pyruvate kinase form rabbit liver against oxidative inactivation," *FEBS Lett.*, vol. 152, 114–118 (1983), reported the protective role of thioltransferase against an inactivated pyruvate kinase by oxidative stress in rabbit liver. G-3PD, a thiol-dependent enzyme may also preserve its activity against oxidation by thioltransferase and GSH in human lung carcinoma cells (Brodie et al., "Cellular recovery of glyceraldehyde-3-phosphate dehydrogenase activity and thiol status after exposure to hydroperoxides," *Arch. Biochem. Biophys.*, vol. 276, 212–218 (1990)). The high oxidation-resistant nature of thioltransferase, coupled with its suggested mechanism of action (Terada et al., "Study on human erythrocyte thioltransferase: Comparative characterization with bovine enzyme and its physiological role under oxidative stress," *J. Biochem.*, vol. 111, 688–692 (1992); Starke et al., "Sensitivity of protein sulfhydryl repair enzymes to oxidative stress," *Free Radical. Biol. & Med.*, vol. 23, 373–384 (1997)) makes it a candidate responsible for repairing the damage induced by oxidative stress. As shown above, lens thioltransferase can dethiolate PSSG and PSSC (more preference to PSSG), similar to thioltransferase in red blood cells (Gravina et al., "Thioltransferase is a specific glutathionyl mixed disulfide oxidoreductase," *Biochemistry*, vol. 32, 3368–3376 (1993)). It is likely that the defense enzymes such as GR, GPx and the energy providing enzyme G-3PD in the cells were all thiolated and inactivated (through SH groups in these enzymes) under the oxidative-stress induced by $H_2O_2$. Thioltransferase, being resistant to oxidation, with the help of adequate levels of cellular GSH and GR, may thus function as a rescuer by dethiolating the inactivated enzymes and restoring their activity. The following Example was performed to determine the role of thioltransferase in restoring G3PD activity after oxidative stress.

Regeneration of G3PD from Rabbit Epithelium Cell Culture after Oxidative Stress 1.6 million of rabbit epithelium cells were exposed to 0.5 mM $H_2O_2$ for 15 minutes. The cells were resuspensed in 2 ml of EDTA pH 8.0 and broken by sonication. After centrifugation, the supernatant was desalted with PD-10 column which equilibrated and eluted with 2 mM EDTA. The elute with G3PD was collected and concentrated with centriprep 3 into about 1 ml for the following regeneration.

Figure 9:
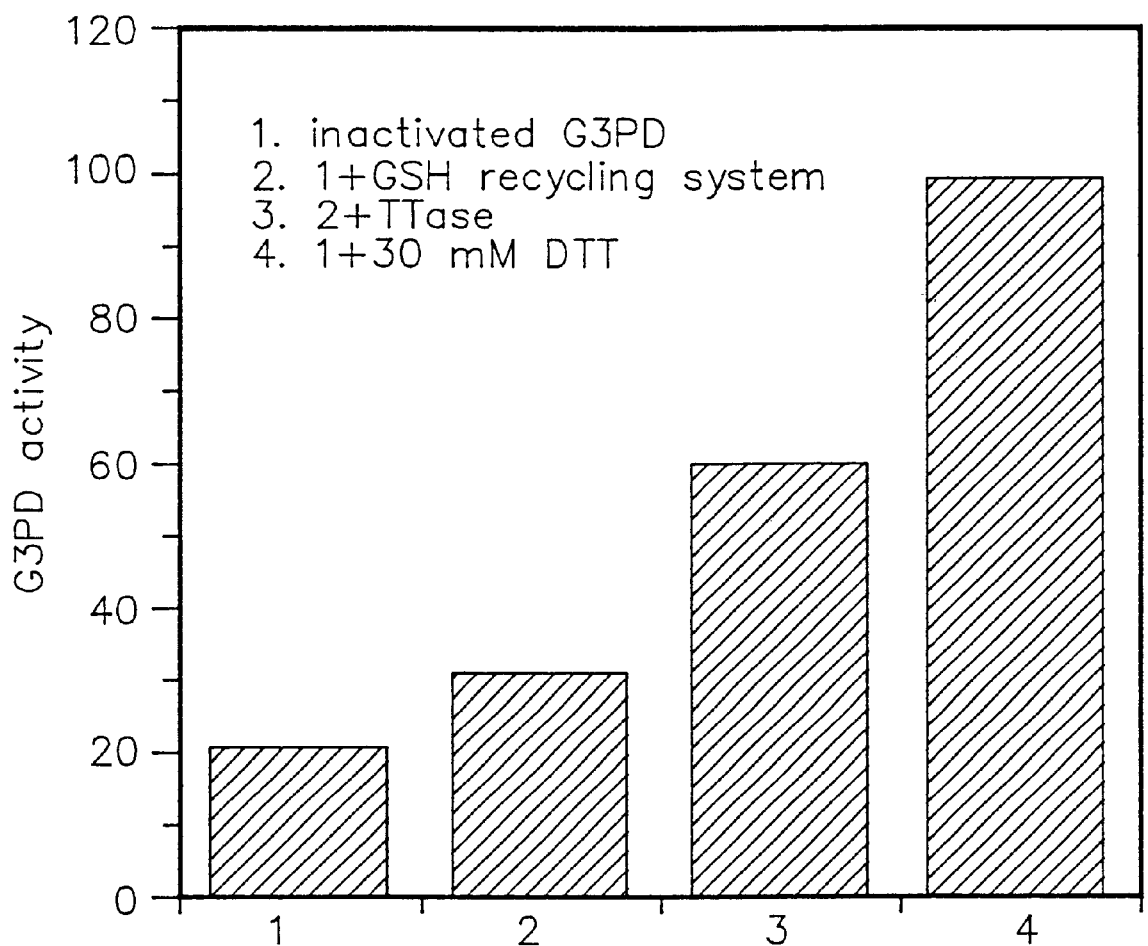
FIG. 9 shows the regeneration of G3PD from $H_2O_2$ (0.5 mM) pretreated rabbit cells by recombinant human lens thioltransferase.
Figure 10:
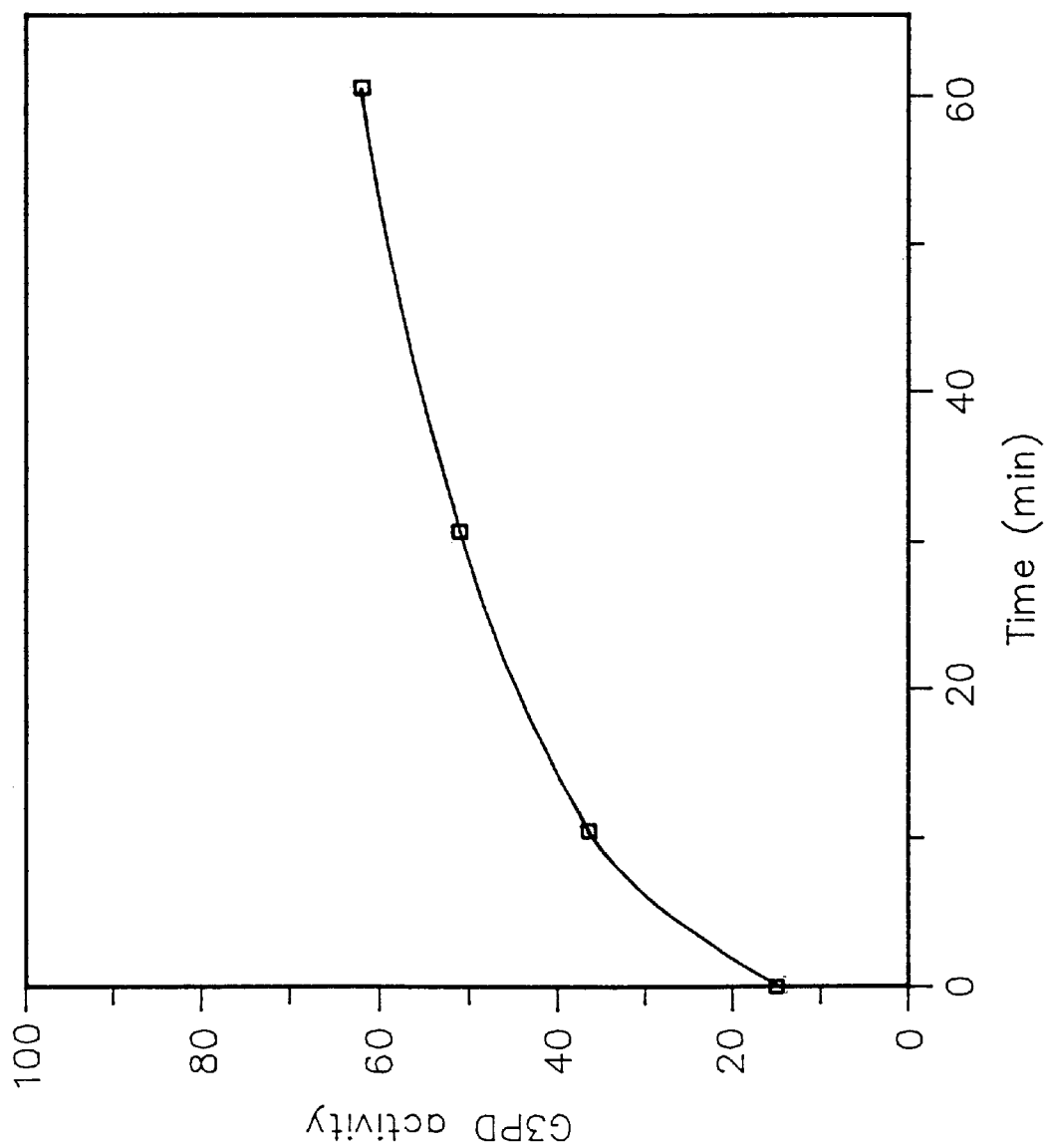
FIG. 10 shows the time dependency of regeneration of G3PD from $H_2O_2$ pretreated rabbit cells by purified recombinant human lens thioltransferase.

100 μL of the above sample was incubated with 0.3 mM NADPH, 1 mM GSH, (stock solutions 2 mM NADPH in 50 mM triethanolamine, pH 7.5 and 5 mM GSH in 50 mM triethanolamine, ph 7.5), 3 U GR/ml and about 0.3 U of recombinant human lens thioltransferase (RHLT) in a total volume of 0.2 ml at 25° C. for 0–60 min. G3PD activity regenerated by GSH recycling system with and without thioltransferase was represented as the percentage of G3PD activity regenerated by 30 mM DTT. The results are shown in FIG. 9. The time dependency of regeneration of G3PD from $H_2O_2$ (0.5 mM) pretreated rabbit cell by purified recombinant human lens thioltransferase is shown in FIG. 10.

The description above should not be construed as limiting the scope of the invention, but as merely providing illustrations to some of the presently preferred embodiments of this invention. In light of the above description and examples, various other modifications and variations will now become apparent to those skilled in the art without departing from the spirit and scope of the present invention as defined by the appended claims. Accordingly, the scope of the invention should be determined solely by the appended claims and their legal equivalents. All references cited herein are hereby incorporated by reference in their entireties.

What is claimed is:

1. A method of inhibiting the formation of a cataract in an eye, which comprises contacting the eye with an effective cataract-inhibiting amount of a human lens thioltransferase (HLTT).

2. The method according to claim 1, wherein said human lens thioltransferase is an expression product of a transformed host cell comprising a DNA molecule coding for HLTT.

3. The method according to claim 1, wherein the eye contains a developing or fully developed cataract.

4. The method according to claim 1, wherein the eye does not contain a developing or fully developed cataract.

5. A method of inhibiting the formation of a cataract in an eye, which comprises administering to the subject a pharmaceutical composition which comprises an effective cataract-inhibiting amount of a human lens thioltransferase.

6. The method according to claim 5, wherein said human lens thioltransferase is an expression product of a transformed host cell comprising a DNA molecule coding for HLTT.

7. The method according to claim 5, wherein the eye contains a developing or fully developed cataract.

8. The method according to claim 5, wherein the eye does not contain a developing or fully developed cataract.

9. The method according to claim 5, wherein the subject is a mammal.

10. The method according to claim 9, wherein the subject is a human.

11. The method according to claim 5, wherein administering the pharmaceutical composition to the subject comprises applying the pharmaceutical composition to the eye of the subject.

12. A method of inhibiting the progression of cataract formation in an eye of a subject which comprises administering to the subject a pharmaceutical composition which comprises an effective cataract-inhibiting amount of a human lens thioltransferase.

13. The method according to claim 12, wherein said human lens thioltransferase is an expression product of a transformed host cell comprising a DNA molecule coding for HLTT.

14. The method according to claim 12, wherein the eye contains a developing or fully developed cataract.

15. The method according to claim 12, wherein the eye does not contain a developing or fully developed cataract.

16. A method of inhibiting the progression of cataract formation in an eye which comprises contacting the eye with an effective cataract-inhibiting amount of a human lens thioltransferase.

17. The method according to claim 16, wherein said human lens thioltransferase is an expression product of a transformed host cell comprising a DNA molecule coding for HLTT.

18. The method according to claim 16, wherein the eye contains a developing or fully developed cataract.

19. The method according to claim 16, wherein the eye does not contain a developing or fully developed cataract.

20. The method according to claim 12, wherein administering the pharmaceutical composition to the subject comprises applying the pharmaceutical composition to the eye of the subject.

21. A method of delaying the onset of cataract formation in an eye of a subject which comprises administering to the subject a pharmaceutical composition which comprises an effective cataract-inhibiting amount of a human lens thioltransferase.

22. The method according to claim 21, wherein said human lens thioltransferase is an expression product of a transformed host cell comprising a DNA molecule coding for HLTT.

23. A method of treating a cataract in an eye of a subject which comprises administering to the subject a pharmaceutical composition which comprises an effective cataract-inhibiting amount of a human lens thioltransferase.

24. The method according to claim 23, wherein said human lens thioltransferase is an expression product of a transformed host cell comprising a DNA molecule coding for HLTT.

* * * * *

UNITED STATES PATENT AND TRADEMARK OFFICE
CERTIFICATE OF CORRECTION

PATENT NO. : 6,379,664 B1  Page 1 of 1
APPLICATION NO. : 09/162564
DATED : April 30, 2002
INVENTOR(S) : Marjorie F. Lou et al.

It is certified that error appears in the above-identified patent and that said Letters Patent is hereby corrected as shown below:

Title page, item [75] inventors: add -- Kuiyi Xing --

Signed and Sealed this

Eleventh Day of September, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,379,664 B1 | Page 1 of 1 |
| APPLICATION NO. | : 09/162564 | |
| DATED | : April 30, 2002 | |
| INVENTOR(S) | : Marjorie F. Lou et al. | |

It is certified that error appears in the above-identified patent and that said Letters Patent is hereby corrected as shown below:

Column 1, lines 6-9 should read as follows:
 "This invention was made with government support under grant number EY010595 awarded by the National Institutes of Health. The government has certain rights to this invention."

Signed and Sealed this

Seventh Day of October, 2008

JON W. DUDAS
*Director of the United States Patent and Trademark Office*

SEQUENCE LISTING

```
<160> NUMBER OF SEQ ID NOS: 9

<210> SEQ ID NO 1
<211> LENGTH: 522
<212> TYPE: DNA
<213> ORGANISM: Homo sapiens
<220> FEATURE:
<221> NAME/KEY: CDS
<222> LOCATION: (4)..(324)

<400> SEQUENCE: 1 gcc atg gct caa gag ttt gtg aac tgc aaa atc cag cct ggg aag gtg      48
```

```
    Met Ala Gln Glu Phe Val Asn Cys Lys Ile Gln Pro Gly Lys Val
     1               5                  10                  15 gta gtt ttc atc aag ccc acc tgc ccc ttc tgc gta aag aca cag gag         96
Val Val Phe Ile Lys Pro Thr Cys Pro Phe Cys Val Lys Thr Gln Glu
                 20                  25                  30 ctc ctc agc caa ttg ccc ttc aaa gaa ggg ctt ctg gaa ttt gtc gat        144
Leu Leu Ser Gln Leu Pro Phe Lys Glu Gly Leu Leu Glu Phe Val Asp
             35                  40                  45 att aca gcc acc agt gac acc aac gag att caa gat tat ctg caa cag        192
Ile Thr Ala Thr Ser Asp Thr Asn Glu Ile Gln Asp Tyr Leu Gln Gln
         50                  55                  60 ctc aca gga gcc aga acg gta cct cgg gtc ttt atc ggt aaa gag tgt        240
Leu Thr Gly Ala Arg Thr Val Pro Arg Val Phe Ile Gly Lys Glu Cys
     65                  70                  75 ata ggt gga tgc act gat cta gaa agt atg cac aag aga ggg gag ctc        288
Ile Gly Gly Cys Thr Asp Leu Glu Ser Met His Lys Arg Gly Glu Leu
 80                  85                  90                  95 ttg acc cgc ctg cag caa att gga gct ctg aaa taa ttacagcaga             334
Leu Thr Arg Leu Gln Gln Ile Gly Ala Leu Lys
                 100                 105 gcagacccaa gctgatagct cccttgagag ctggatggca gtgcagataa tgacagcgct      394
tcctggtgga tggatgccgg gctaccttca ctcagctgca actactgttt acttaaaaat      454
tctgaaatgt gttaacccaa ataattgggg ggagtgggtt ttgggggaca aaacagattt      514
ttcttctg                                                               522

<210> SEQ ID NO 2
<211> LENGTH: 106
<212> TYPE: PRT
<213> ORGANISM: Homo sapiens

<400> SEQUENCE: 2

Met Ala Gln Glu Phe Val Asn Cys Lys Ile Gln Pro Gly Lys Val Val
 1               5                  10                  15

Val Phe Ile Lys Pro Thr Cys Pro Phe Cys Val Lys Thr Gln Glu Leu
             20                  25                  30

Leu Ser Gln Leu Pro Phe Lys Glu Gly Leu Leu Glu Phe Val Asp Ile
         35                  40                  45

Thr Ala Thr Ser Asp Thr Asn Glu Ile Gln Asp Tyr Leu Gln Gln Leu
     50                  55                  60

Thr Gly Ala Arg Thr Val Pro Arg Val Phe Ile Gly Lys Glu Cys Ile
 65                  70                  75                  80

Gly Gly Cys Thr Asp Leu Glu Ser Met His Lys Arg Gly Glu Leu Leu
                 85                  90                  95

Thr Arg Leu Gln Gln Ile Gly Ala Leu Lys
                 100                 105

<210> SEQ ID NO 3
<211> LENGTH: 106
<212> TYPE: PRT
<213> ORGANISM: Sus scrofa

<400> SEQUENCE: 3

Met Ala Gln Ala Phe Val Asn Ser Lys Ile Gln Pro Gly Lys Val Val
 1               5                  10                  15

Val Phe Ile Lys Pro Thr Cys Pro Phe Cys Arg Lys Thr Gln Glu Leu
             20                  25                  30

Leu Ser Gln Leu Pro Phe Lys Glu Gly Leu Leu Glu Phe Val Asp Ile
```

-continued

```
                 35                  40                  45

Thr Ala Thr Ser Asp Thr Asn Glu Ile Gln Asp Tyr Leu Gln Gln Leu
         50                  55                  60

Thr Gly Ala Arg Thr Val Pro Arg Val Phe Ile Gly Lys Glu Cys Ile
 65                  70                  75                  80

Gly Gly Cys Thr Asp Leu Glu Ser Met His Lys Arg Gly Glu Leu Leu
                 85                  90                  95

Thr Arg Leu Gln Gln Ile Gly Ala Leu Lys
            100                 105

<210> SEQ ID NO 4
<211> LENGTH: 106
<212> TYPE: PRT
<213> ORGANISM: Homo sapiens

<400> SEQUENCE: 4

Met Ala Gln Glu Phe Val Asn Cys Lys Ile Gln Pro Gly Lys Val Val
  1               5                  10                  15

Val Phe Ile Lys Pro Thr Cys Pro Tyr Cys Arg Arg Ala Gln Glu Ile
                 20                  25                  30

Leu Ser Gln Leu Pro Ile Lys Gln Gly Leu Leu Glu Phe Val Asp Ile
                 35                  40                  45

Thr Ala Thr Asn His Thr Asn Glu Ile Gln Asp Tyr Leu Gln Gln Leu
         50                  55                  60

Thr Gly Ala Arg Thr Val Pro Arg Val Phe Ile Gly Lys Asp Cys Ile
 65                  70                  75                  80

Gly Gly Cys Ser Asp Leu Val Ser Leu Gln Gln Ser Gly Glu Leu Leu
                 85                  90                  95

Thr Arg Leu Lys Gln Ile Gly Ala Leu Gln
            100                 105

<210> SEQ ID NO 5
<211> LENGTH: 105
<212> TYPE: PRT
<213> ORGANISM: Bos taurus

<400> SEQUENCE: 5

Met Ala Gln Ala Phe Val Asn Ser Lys Ile Gln Pro Gly Lys Val Val
  1               5                  10                  15

Val Phe Ile Lys Pro Thr Cys Pro Tyr Cys Arg Lys Thr Gln Glu Leu
                 20                  25                  30

Leu Ser Gln Leu Pro Phe Lys Gln Leu Leu Glu Phe Val Asp Ile Thr
                 35                  40                  45

Ala Ala Gly Asn Ile Ser Glu Ile Gln Asp Tyr Leu Gln Gln Leu Thr
         50                  55                  60

Gly Ala Arg Thr Val Pro Arg Val Phe Ile Gly Gln Glu Cys Ile Gly
 65                  70                  75                  80

Gly Cys Thr Asp Leu Val Asn Met His Glu Arg Gly Glu Leu Leu Thr
                 85                  90                  95

Arg Leu Lys Gln Met Gly Ala Leu Gln
            100                 105

<210> SEQ ID NO 6
<211> LENGTH: 107
<212> TYPE: PRT
<213> ORGANISM: Oryctolagus cuniculus

<400> SEQUENCE: 6
```

-continued

```
Met Ala Gln Glu Phe Val Asn Ser Lys Ile Gln Pro Gly Lys Val Val
 1               5                  10                  15

Val Phe Ile Lys Pro Thr Cys Pro Tyr Cys Arg Lys Thr Gln Glu Ile
            20                  25                  30

Leu Ser Gln Leu Pro Phe Lys Gln Gly Leu Leu Glu Phe Val Asp Ile
        35                  40                  45

Thr Ala Thr Ser Asp Met Ser Glu Ile Gln Asp Tyr Leu Gln Gln Leu
    50                  55                  60

Thr Gly Ala Arg Thr Val Pro Arg Val Phe Leu Gly Lys Asp Cys Ile
 65                 70                  75                  80

Gly Gly Cys Ser Asp Leu Ile Ala Met Gln Glu Lys Gly Glu Leu Leu
                85                  90                  95

Ala Arg Leu Lys Glu Met Gly Ala Leu Arg Gln
            100                 105

<210> SEQ ID NO 7
<211> LENGTH: 85
<212> TYPE: PRT
<213> ORGANISM: Escherichia coli

<400> SEQUENCE: 7

Met Gln Thr Val Ile Phe Gly Arg Ser Gly Cys Pro Tyr Cys Val Arg
 1               5                  10                  15

Ala Lys Asp Leu Ala Glu Lys Leu Ser Asn Glu Arg Asp Asp Phe Gln
            20                  25                  30

Tyr Gln Tyr Val Asp Ile Arg Ala Glu Gly Ile Thr Lys Glu Asp Leu
        35                  40                  45

Gln Gln Lys Ala Gly Lys Pro Val Glu Thr Val Pro Gln Ile Phe Val
    50                  55                  60

Asp Gln Gln His Ile Gly Gly Tyr Thr Asp Phe Ala Ala Trp Val Lys
 65                 70                  75                  80

Glu Asn Leu Asp Ala
                85

<210> SEQ ID NO 8
<211> LENGTH: 21
<212> TYPE: DNA
<213> ORGANISM: Sus scrofa

<400> SEQUENCE: 8
agcatggctc aagcatttgt g                                              21

<210> SEQ ID NO 9
<211> LENGTH: 24
<212> TYPE: DNA
<213> ORGANISM: Sus scrofa

<400> SEQUENCE: 9
gaagaaaaat ctgttttgtc cccc                                           24
```